United States Patent [19]
Magda et al.

[11] Patent Number: 6,022,959
[45] Date of Patent: Feb. 8, 2000

[54] NUCLEIC ACIDS INTERNALLY-DERIVATIZED WITH A TEXAPHYRIN METAL COMPLEX AND USES THEREOF

[75] Inventors: Darren Magda, Cupertino; Shaun P. Crofts, Campbell; Meredith Wright, San Jose, all of Calif.

[73] Assignee: Pharmacyclics, Inc., Sunnyvale, Calif.

[21] Appl. No.: 08/975,522

[22] Filed: Nov. 20, 1997

Related U.S. Application Data

[63] Continuation of application No. PCT/US97/14682, Aug. 20, 1997.
[60] Provisional application No. 60/077,185, Aug. 20, 1996.
[51] Int. Cl.$^7$ .................................................. C07H 21/02
[52] U.S. Cl. .................... 536/23.1; 536/22.1; 536/25.3; 536/25.31; 536/25.32; 536/25.34; 534/11; 534/13; 534/15; 534/16; 540/149; 540/465; 540/472
[58] Field of Search .................... 536/22.1, 23.1, 536/25.3, 25.31, 25.34, 25.32; 534/11, 13, 15, 16; 540/149, 465, 472

[56] References Cited

U.S. PATENT DOCUMENTS

| | | |
|---|---|---|
| 4,935,498 | 6/1990 | Sessler et al. . |
| 5,135,717 | 8/1992 | Renzoni et al. . |
| 5,216,141 | 6/1993 | Benner . |
| 5,252,720 | 10/1993 | Sessler et al. . |
| 5,257,970 | 11/1993 | Dougherty . |
| 5,272,056 | 12/1993 | Burrows et al. . |
| 5,292,414 | 3/1994 | Sessler et al. . |
| 5,457,183 | 10/1995 | Sessler et al. . |
| 5,559,207 | 9/1996 | Sessler et al. . |
| 5,565,552 | 10/1996 | Magda et al. . |
| 5,567,687 | 10/1996 | Magda et al. . |
| 5,578,718 | 11/1996 | Cook et al. . |
| 5,580,543 | 12/1996 | Sessler et al. . |
| 5,587,371 | 12/1996 | Sessler et al. . |
| 5,594,136 | 1/1997 | Sessler et al. . |
| 5,595,726 | 1/1997 | Magda et al. . |
| 5,599,923 | 2/1997 | Sessler et al. . |
| 5,599,928 | 2/1997 | Hemmi et al. . |
| 5,607,924 | 3/1997 | Magda et al. . |
| 5,622,946 | 4/1997 | Sessler et al. . |
| 5,672,490 | 9/1997 | Sessler et al. . |
| 5,714,328 | 2/1998 | Magda et al. . |

FOREIGN PATENT DOCUMENTS

| | | |
|---|---|---|
| 0214908 A1 | 3/1987 | European Pat. Off. . |
| 2697254 | 4/1994 | France . |
| WO 98/07733 | of 0000 | WIPO . |
| WO 90/02747 | 3/1990 | WIPO . |
| WO 90/10633 | 9/1990 | WIPO . |
| 91/19730 | 12/1991 | WIPO . |
| WO 94/29316 | 12/1994 | WIPO . |
| WO 95/10307 | 4/1995 | WIPO . |
| WO 95/21845 | 8/1995 | WIPO . |
| WO 95/29702 | 9/1995 | WIPO . |
| WO 95/26733 | 10/1995 | WIPO . |
| WO 96/07667 | 3/1996 | WIPO . |
| WO 96/09315 | 3/1996 | WIPO . |
| WO 96/38461 | 12/1996 | WIPO . |
| WO 96/40253 | 12/1996 | WIPO . |

OTHER PUBLICATIONS

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate "Porphyrin–Like" Ligands", *Comm. Inorg. Chem.*, 7:333–350, 1988.

Sessler et al., "An "Expanded Porphyrin": The Synthesis and Structure of a New Aromatic Pentadentate Ligand", *J. Am. Chem. Soc.*, 110:5586–5588, 1988.

Sessler et al., "A Water–Stable Gadolinium (III) Complex Derived from a New Pentadentate "Expanded Porphyrin" Ligand", *Inorg. Chem.*, 28:3390–3393, 1989.

Sessler et al., "Binding of Pyridine and Benzimidazole to a Cadmium "Expanded Porphyrin": Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate Expanded Porphyrin" Ligand, *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived ("Texaphyrin"–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin': A Novel 22 π–Electron Aromatic Pentadentate Macrocyclic Ligand", *ACS meeting*, Los Angeles, Sep. 1988.

(List continued on next page.)

*Primary Examiner*—James O. Wilson
*Attorney, Agent, or Firm*—Akin, Gump, Strauss, Hauer & Feld, L.L.P.

[57] ABSTRACT

Texaphyrin metal complex-oligonucleotide and -oligonucleotide analog conjugates are provided where the texaphyrin is bound to an internal linkage of the oligonucleotide or oligonucleotide analog, the conjugates having catalytic activity for the hydrolysis of ribonucleic acid. Further, conjugates demonstrating catalytic turnover are described, the conjugates being especially effective under conditions where the concentration of RNA target exceeds that of available conjugate.

25 Claims, 5 Drawing Sheets

OTHER PUBLICATIONS

Sessler and Burrell, "Expanded Porphyrins," *Topics in Current Chemistry,* 161:180–273, 1991.

Sessler et al., "Synthesis and Structural Characterization of Lanthanide (III) Texaphyrins," *Inorganic Chemistry,* 32(14):3175–3187, 1993.

Sessler et al., "Preparation of Lanthanide (III) Texaphyrin Complexes and Their Applications to Magnetic Resonance Imaging and Photodynamic Therapy," *Abstracts of Papers,* Part 1, 204th ACS National Meeting, Aug. 23–28, 1992, Washington, DC.

Sessler et al., "Synthesis and Applications of Schiff–Base Derived Expanded Porphyrins," *Abstracts of Papers,* Part 1, 204th ACS National Meeting, Aug. 23–28, 1992, Washington, DC.

Sessler, Jonathan L., "Texas–Sized Molecule," *Discovery,* 13(1):44–49, 1993.

Sessler et al., "Photodynamic Inactivation of Enveloped Viruses Using Sapphyrin, a 22 π–Electron "Expanded Porphyrin": Possible Approaches to Prophylactic Blood Purification Protocols," *SPIE Photodynamic Therapy: Mechanisms II.* 1203:233–245, 1990.

Maiya et al., "Ground– and Excited–State Spectral and Redox Properties of Cadmium(II) Texaphyrin," *Journal of Physical Chemistry,* 93(24):8111–8115, 1989.

Sessler et al., "Texaphyrins: Synthesis and Applications," *Accounts of Chemical Research,* 27(2):43–50, 1994.

Leff, "Texas 'Son–of–Porphyrin' Molecule Lassos Europium to Kill Drug Resistance Gene," *BioWorld Today,* 5(156):1, 1994.

Young et al., "Preclinical Evaluation of Gadolinium (III) Texaphyrin Complex. A New Paramagnetic Contrast Agent for Magnetic Resonance Imaging," *Investigative Radiology,* 29(3):330–338, 1994.

Furuta et al., "Enhanced Transport of Nucleosides and Nucleoside Analogues with Complementary Base–Pairing Agents," *Journal of the American Chemical Society,* 1991, 113:4706–4707.

Sessler et al., "Anion Binding: A New Direction in Porphyrin–related Research," *Pure & Applied Chem.,* 65(3):393–398, 1993.

T.D. Mody et al., "Lutetium (III) Texaphyrin: A Novel Photodynamic Therapy Agent," Abstract, *22nd Annual American Society for Photobiology,* Scottsdale, AZ, Jun. 25–29, 1994.

Sessler et al., "Gadolinium (III) Texaphyrin: A Novel MRI Contrast Agent," *Journal of the American Chemical Society,* 115(22):10, 368–10, 369, 1993.

Iverson et al., "Interactions Between Expanded Porphyrins and Nucleic Acids," *Pure Applied Chemistry,* 66(4):845–850, 1994.

Magda et al., "Site–Specific Hydrolysis of RNA by Europium (III) Texaphyrin Conjugated to a Synthetic Oligodeoxyribonucleotide," *Journal of the American Chemical Society,* 116(16):7439–7440, 1994.

Goodchild, John, "Conjugates of Oligonucleotides and Modified Oligonucleotides: A Review of Their Synthesis and Properties," *Bioconjugate Chemistry,* 1(3):165–187, 1990.

Mastruzzo et al., "Targeted Photochemical Modification of HIV–Derived Oligoribonucleotides by Antisense Oligodeoxynucleotides Linked to Porphyrins," *Photochem. Photobiol.,* 60(4):316–322, 1994.

Teare and Wollenzien, "Specificity of Site Directed Psoralen Addition to RNA," *Nucleic Acids Res.,* 17(9):3359–3372, 1989.

Agrawal and Tang, "Efficient Synthesis of Oligoribonucleotide and Its Phosphorothioate Analogue Using H–Phosphonate Approach," *Tetrahedron Letters,* 31(52):7541–7544, 1990.

Breslow et al., "Effects of Metal Ions, Including $Mg^{2+}$ and Lanthanides, on the Cleavage of Ribonucleotides and RNA Model Compounds," *Proc. Natl. Acad. Sci. USA,* 88:4080–4083, 1991.

Cohen, Jack S., "Chemically Modified Oligodeoxynucleotide Analogs as Regulators of Viral and Cellular Gene Expression," *Gene Regulation: Biology of Antisense RNA and DNA,* 247–259, 1992.

Morrow et al., "Efficient Catalytic Cleavage of RNA by Lanthanide(III) Macrocyclic Complexes: Toward Synthetic Nucleases for in Vivo Applications," *J. Am. Chem. Soc.,* 114:1903–1905, 1992.

Shelton and Morrow, "Catalytic Transesterification and Hydrolysis of RNA by Zinc(II) Complexes," *Inorganic Chemistry,* 30:4295–4299, 1991.

Stern et al., "Hydrolysis of RNA by Transition–Metal Complexes," *J. Am. Chem. Soc.,* 112:5357–5359, 1990.

Kolasa et al., "Trivalent Lanthanide Ions Do Not Cleave RNA in DNA–RNA Hybrids", *Inorg. Chem.,* 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.,* 32(12):1716–1719, 1993.

Hayashi et al., "Site–Selective Hydrolysis of tRNA by Lanthanide Metal Complexes," *Inorg. Chem.,* 32:5899–5900, 1993.

Magda et al., "Sequence–Specific Photocleavage of DNA by an Expanded Porphyrin with Irradiation Above 700 nm," *J. Am. Chem. Soc.,* 117:3629–3630, 1995.

Sessler et al., "Expanded Porphyrins. Receptors for Cationic, Anionic, and Neutral Substrates," in Transition Metals in Supramolecular Chemistry, L. Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 1994.

International Search Report mailed Feb. 22, 1994.

International Search Report mailed Feb. 3, 1994.

International Search Report mailed Feb. 9, 1996.

Casas et al., "Preparation of Hybrid "DNA Cleaver–Oligonucleotide"Molecules Based on a Metaallotris (methylpyridiniumyl) porphyrin Motif," Bioconjugate Chem., vol. 4, No. 5, pp. 366–371, Sep./Oct. 1993.

Magda et al., "Texaphyrin–based nuclease analogs. Rationally designed approaches to the catalytic cleavage of RNA and DNA targets," *Chemical Abstracts* 125 (7) : 5032 (Aug. 1996).

International Search Report mailed Dec. 17, 1996.

Sessler et al., "Synthesis and Binding Properties of Monomeric and Dimeric Guanine and Cytosine Amine Derivatives," *J. Org. Chem.,* 1992, 57:818–826.

Bashkin et al., "Sequence–Specific Cleavage of HIV mRNA by a Ribozyme Mimic," *J. Am. Chem. Soc.* 116:5981–5982 (1994).

Gura, T., "Antisense Has Growing Pains," Science 270:575–577 (1995).

Hall et al., Efficient Sequence–Specific Cleavage of RNA Using Novel Europium Complexes Conjugated to Oligonucleotides, Chemistry & Biology 1(3):185–190 (1994).

Hall et al., "Towards Artificial Ribonucleases: The Sequence–Specific Cleavage of RNA in a Duplex," Nucleic Acids Research 24(18):3522–3526 (Sep. 1996).

Haner et al., "Sequence–Specific Cleavage of RNA Using Lanthanide Complexes Linked to Oligonucleotides," Proceeds of NATO Advanced Research Workshop on DNA and RNA Cleavers and Chemotherapy of Cancer and Viral Diseases, B. Neunier, Ed., Kluwer Academic Publishers, Netherlands (Sep. 1995).

James, W., "Towards Gene–Inhibition Therapy: A Review of Progress and Prospects in the Field of Antiviral Antisense Nucleic Acids and Ribozymes," Antiviral Chemistry & Chemotherapy, 2(4):191–214 (1991).

Manchanda et al., "Automated Solid–Phase Synthesis of Site–Specifically Platinated Oligodeoxyribonucleotides," *J. Am. Chem. Soc.* 118:5144–5145 (May 1996).

Mestre et al., "Preparation and Nuclease Activity of Hybrid 'Metallotris (methylpyridinium) porphyrin Oligonucleotide' Molecules Having a 3'–Loop for Protection Against 3'–Exonucleases" *Bioconjugate Chem.* 6:466–472 (Jul. 1995).

Reynolds et al., "Antisense Oligonucleotides Containing an Internal, Non–Nucleotide–Based Linker Promote Site–Specific Cleavage of RNA," Nucleic Acids Research 24(4):760–765 (Feb. 1996).

Uhlmann et al., "Antisense Oligonucleotides: A New Therapeutic Principle," *Chemical Reviews,* 94(4):544–584 (1990).

BioGenex, DNA & RNA Synthesis Products, Catalog for 1994–95, p. 18.

Chandler, C., Correspondence from Clontech dated Jun. 5, 1996.

Press Release from Pharmacyclics dated Aug. 26, 1996.

PCT/US90/01208 International Search Report mailed Aug. 2, 1990.

PCT/US96/08262 International Search Report mailed Sep. 10, 1996.

Magda, et al., " Synthesis and Kinetic Properties of Ribozyme Analogues Prepared Using Phosphoramidite Derivatives of Dysprosium (III) Texaphyrin," *J. Am. Chem. Soc.,* 119:2293–2294, 1997.

Search to "Genta" Patent, Jun. 21, 1996.

International Search Report for related foreign application PCT/US96/09419, date of mailing Dec. 17, 1996.

PCT/US97/14682 International Search Report mailed Dec. 18, 1997.

Casas, et al., "New conjugate of Oligo–nucleotide and Cationic Metallo–Porphyrin Cleave Complementary Nucleic Acid Selectively, Useful as Antitumor, Antiviral, Antibacterial and Antiparasitic Agent" (Abstract).

LeDoan et al., "Targeted Cleavage of Polynucleotides by Complementary Oligonucleotides Covalently Linked to Iron–Porphyrins," *Biochemistry,* 25: 6736–6739, 1986.

Magda, et al., "Metal Complex Conjugates of Antisense DNA Which Display Ribozyme–Like Activity," *J. Am. Chem. Soc.,* 119:6947–6948, 1997.

NUCLEIC ACIDS INTERNALLY-DERIVATIZED WITH A TEXAPHYRIN METAL COMPLEX AND USES THEREOF

This application is a continuation application of copending international application PCT/US971/14682 filed Aug. 20, 1997, which claims priority to U.S. Pat. No. 60/077,185, filed Aug. 20, 1996. This applications are incorporated by reference herein.

BACKGROUND OF THE INVENTION

Texaphyrins are aromatic pentadentate macrocyclic "expanded porphyrins" useful as MRI contrast agents, as radiosensitizers and in photodynamic therapy (PDT). They have activity for phosphate ester and ribonucleic acid (RNA) hydrolysis, or in RNA and deoxyribonucleic acid (DNA) light-induced cleavage. Texaphyrin is considered as being an aromatic benzannulene containing both $18\pi$- and $22\pi$-electron delocalization pathways. See, e.g., Sessler, J. L. et al., *Accounts of Chemical Research,* 1994, 27:43. Texaphyrin molecules absorb strongly in the tissue-transparent 730–900 nm range, and they exhibit inherent selective uptake or biolocalization in certain tissues, particularly regions such as, for example, liver, atheroma or tumor tissue. Texaphyrins and water-soluble texaphyrins, method of preparation and various uses have been described in U.S. Pat. Nos. 4,935,498; 5,162,509; 5,252,720; 5,256,399; 5,272,142; 5,292,414; 5,369,101; 5,432,171; 5,439,570; 5,451,576; 5,457,183; 5,475,104 5,504,205; 5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; and 5,622,946; PCT publications WO 90/10633, 94/29316, 95/10307, 95/21845, 96/09315; 96/38461, and 96/40253; allowed U.S. patent application Ser. Nos. 08/484,551, 08/591,318; and 08/624,311; and pending U.S. patent application Ser. Nos. 08/458,347; 08/700,277; 08/763,451; each patent, publication, and application is incorporated herein by reference.

Texaphyrins may be coupled to site-directing molecules to form conjugates for targeted in vivo delivery. Site-specific light-induced photocleavage of DNA with a diamagnetic metal texaphyrin complex-oligonucleotide conjugate has been carried out; see, Magda, D. et al., *J. Am. Chem. Soc.* 1995, 117:3629; and WO 96/09315 (the entire disclosure of which is incorporated herein by reference). Site-specific ester hydrolysis of RNA with a lanthanide metal texaphyrin complex-oligonucleotide conjugate has been shown; see, Magda, D. et al., *J. Am. Chem. Soc.,* 1994, 116:7439; and PCT publication WO 94/29316 (the entire disclosure of which is incorporated herein by reference). Hydrolysis was observed when the complex was covalently bound to an end of the oligonucleotide, but hydrolysis was not observed when the complex was covalently bound to a 5 position of an internal thymine residue. Therefore, it has not been previously shown that a texaphyrin metal complex-oligonucleotide conjugate where the texaphyrin is covalently bound to an internal linkage of the oligonucleotide would hydrolyze RNA. That such a conjugate would be available for further hydrolytic cleavage (i.e., exhibiting "turnover") also has not been shown. Such an RNA hydrolysis catalyst would be very useful since much smaller amounts would be needed. This is especially important in in vivo or ex vivo treatment situations where it is desirable for only a relatively small amount of therapeutic agent to be present, or where only a fraction of the agent may be able to access a treatment site. It is also desirable where the metal complex or the oligonucleotide is quite expensive or can be produced in only small quantities.

PCT publication WO 94/15619 relates to acid-resistant oligonucleotides containing 2'-O-alkyl ribosyl groups or methylphosphonate internucleoside links, reportedly useful for oral delivery in antisense or triple strand therapy. U.S. Pat. No. 5,216,141 relates to nucleotide analogues and oligonucleotide analogues with sulfide, sulfoxide, or sulfone linking groups to impart stability to chemical or enzymatic hydrolysis. French publication 2 697 254 relates to conjugates comprising an oligonucleotide and a derivative of a metalloporphyrin cation that appear to function via oxidative cleavage of a target nucleic acid rather than by hydrolytic cleavage.

Reynolds et al., (*Nucleic Acids Research,* 24:760–765, 1996) relate to antisense oligonucleotides containing an internal, non-nucleotide-based linker bound to a cleaver molecule for site-specific cleavage of RNA. Because of low binding affinities, cleavage was carried out at 25° C. and was reported at less than about 10% after 5 days incubation, a rate that is clearly insufficient for biological application. Furthermore, such agents would be unstable at a body temperature of 37° C. Similarly, PCT publication WO 95/26733 relates to oligonucleoside cleavage compounds where the incubations were conducted at 25° C. over periods ranging from 2–5 days. Bashkin et al. (*J. Am. Chem. Soc.* 1994, 116:59811–5982 and WO 91/19730) relate to hydrolysis of RNA at rates of 18–25% after 72 h at 45° C. by a ribozyme mimic. These rates are also too slow for biological applications.

PCT publication, WO 96/07667, relates to oligonucleotide conjugates, compositions, and methods for splitting ribonucleic acids. A transesterification or hydrolysis catalyst is bonded to the oligonucleotide, and the inner sequence of the oligonucleotide is partially noncomplementary to a naturally occurring target RNA. Terpyridine-derived lanthanide complex stability, biodistribution, and toxicity are unknown.

Due to advantages to the use of texaphyrins as pharmaceutical agents, the present inventors provide herein texaphyrin metal complex-oligonucleotide conjugates or oligonucleotide analog conjugates having hydrolytic activity for RNA and demonstrate that that activity is catalytic with turnover under reaction conditions having excess substrate.

SUMMARY OF THE INVENTION

The present invention relates to compositions and methods for hydrolysis of ribonucleic acid. More particularly, it concerns oligonucleotide or oligonucleotide analog conjugates of a texaphyrin metal complex where the texaphyrin is bound to an internal linkage in the oligonucleotide or oligonucleotide analog, the conjugates having said hydrolytic activity.

The present invention results from the discovery that texaphyrin metal complex-oligonucleotide and -oligonucleotide analog conjugates, where the texaphyrin is bound to an internal linkage of the conjugate, have hydrolytic activity for RNA. The RNA substrate has at least partial sequence complementarity to the oligonucleotide or oligonucleotide analog and, more preferably, the RNA has near complete sequence complementarity to the oligonucleotide or oligonucleotide analog. The RNA substrate may contain loops or bulges, abasic sites, and/or mismatches or other non-base-paired regions. The internal linkage is a linkage that allows hydrolytic cleavage of the target RNA, and most preferably, allows cleavage across the minor groove of an RNA-nucleic acid duplex molecule. Preferred linkages include a 2' linkage to an internal ribose moiety of a ribonucleic acid residue of the oligonucleotide, or a linkage to an internal branching linker of an oligonucleotide analog, for example.

The present invention further provides texaphyrin metal complex-oligonucleotide and -oligonucleotide analog conjugates that exhibit catalytic turnover as evidenced by hydrolytic reactions of RNA carried out under reaction conditions having excess substrate.

A method for synthesizing a texaphyrin metal complex-oligonucleotide conjugate having the texaphyrin metal complex bound to an internal ribonucleotide residue is a further aspect of the invention. The method comprises the step of coupling a 2' hydroxyl of a ribonucleotide residue internal to the oligonucleotide to an amidite derivative of a texaphyrin metal complex.

A further aspect of the present invention is a method for synthesizing a texaphyrin metal complex-oligonucleotide analog conjugate having the texaphyrin metal complex bound to a branching linker internal to the oligonucleotide analog. The method comprises the step of coupling the branching linker to an amidite derivative of a texaphyrin metal complex.

A method of hydrolyzing ribonucleic acid under reaction conditions having excess conjugate is a further aspect of the invention. The method comprises contacting the ribonucleic acid with a conjugate of a texaphyrin metal complex-oligonucleotide or -oligonucleotide analog where the texaphyrin is bound to an internal linkage of the oligonucleotide or oligonucleotide analog; and incubating the ribonucleic acid and the conjugate under reaction conditions having excess conjugate and for a time sufficient to hydrolyze a phosphate ester bond of the ribonucleic acid.

A method of hydrolyzing ribonucleic acid under reaction conditions having excess substrate is also an aspect of the invention. The method comprises contacting the ribonucleic acid with a conjugate of the present invention wherein the hydrolytic cleavage activity for the ribonucleic acid produces ribonucleic acid products that diffuse away from the conjugate, or are displaced by another substrate, leaving the conjugate free to catalyze another cleavage reaction; and incubating the ribonucleic acid and the conjugate under substrate excess reaction conditions and for a time sufficient to hydrolyze a phosphate ester bond of the ribonucleic acid and allow turnover of the conjugate.

Use of a conjugate comprising a texaphyrin metal complex bound to an internal linkage of an oligonucleotide or oligonucleotide analog, the conjugate having hydrolytic cleavage activity for ribonucleic acid, in the preparation of a pharmaceutical composition for use in hydrolytic cleavage of ribonucleic acid or for treatment of a human subject is a further aspect of the invention.

Following long-standing patent law convention, the terms "a" and "an" mean "one or more" when used in this application, including the claims.

ABBREVIATIONS

CED: β-Cyanoethyl diisopropyl protecting group
DMT: Dimethoxytrityl protecting group
DyTx: A texaphyrin bound to the metal dysprosium
N-PAC: Amino protecting phenoxyacetyl group
THF: Tetrahydrofuran

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
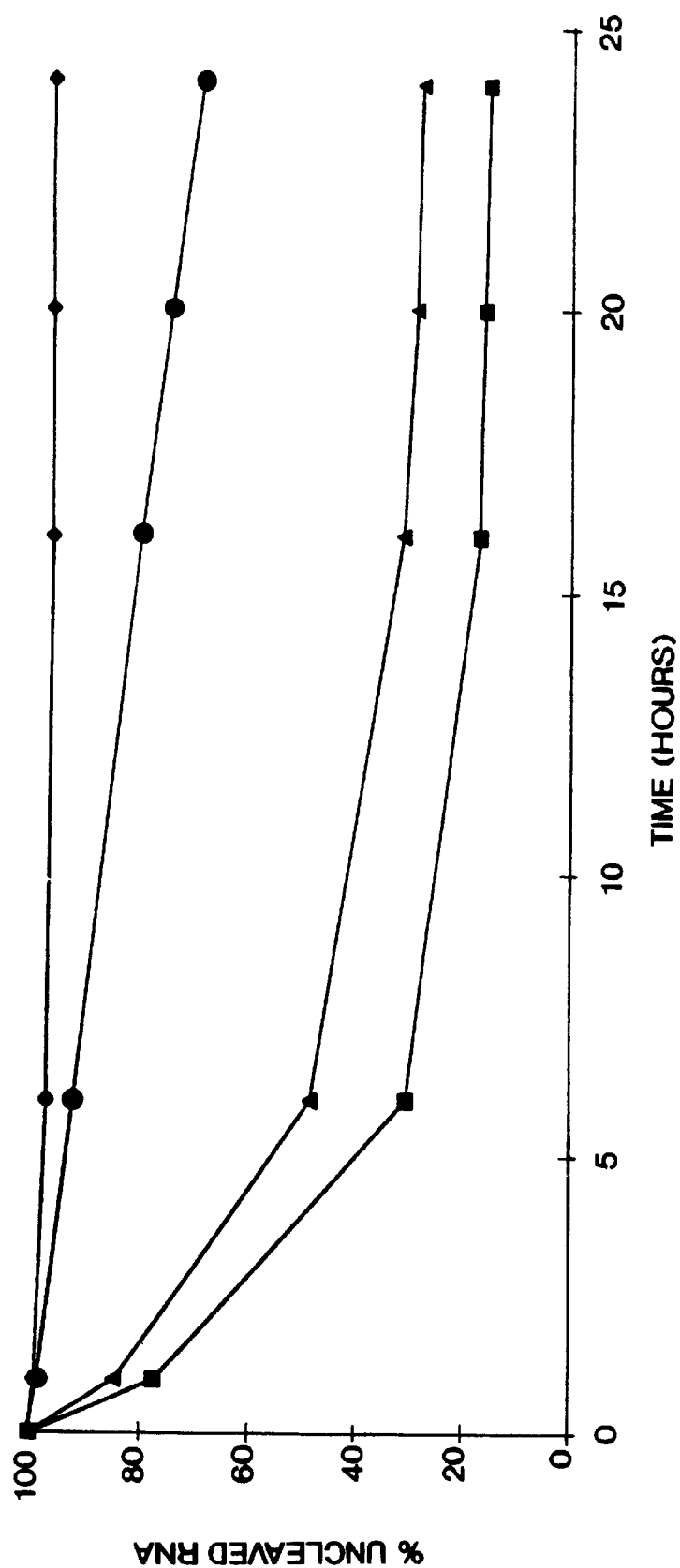
FIG. 1 provides data for site-specific hydrolysis of 5'-$^{32}$P labeled RNA using an oligonucleotide end-derivatized with a dysprosium texaphyrin (■, no added RNA; and ♦, with 250 nM added unlabeled RNA) and an oligonucleotide internally-derivatized with a dysprosium texaphyrin (▲, no added RNA; and ●, with 250 nM added unlabeled RNA).

The present invention discloses texaphyrin metal complex-oligonucleotide and -oligonucleotide analog conjugates where the texaphyrin is bound to an internal linkage of the oligonucleotide or oligonucleotide analog, the conjugates having catalytic activity for the hydrolysis of ribonucleic acid. Previously, a conjugate where the texaphyrin was bound to an internal thymine residue failed to effect hydrolysis (WO 94/29316). The present inventors have constructed conjugates having RNA hydrolytic activity, and believe that the prior conjugate was ineffective possibly because it was not positioned to reach into the minor groove of the DNA-RNA duplex to effect catalysis and/or complete complementarity of the RNA target sequence with the sequence of the oligonucleotide conjugate discouraged catalysis. Attachment of texaphyrin to a different position of the base or attachment to the 5'-3' backbone of a conjugate as provided in the compositions of the present invention appears to be important for catalysis to occur. Not wanting to be bound by theory, it is believed that the initial reaction catalyzed by the texaphyrin metal complex is a transesterification reaction that forms a reactive cyclic phosphate intermediate; the intermediate then reacts with water. The overall reaction is thus hydrolysis of the phosphate diester and the term "hydrolysis" is used herein to describe the overall reaction. This hydrolytic reaction is not dependent on the presence or absence of light.

The RNA may be a solution or a suspension of RNA or may be cellular RNA in vitro, in vivo, or ex vivo. The ability to hydrolyze and cleave RNA has important implications for the treatment of various diseases; for destruction of retroviral RNA, messenger RNA, ribosomal RNA, RNA cofactors, transfer RNA, small nuclear RNA, and small cytoplasmic RNA, thereby providing a multifactorial approach to eliminating diseased, cancerous or other unwanted cells or tissues. Use of conjugates of the present invention in ex vivo or in vitro blood purification protocols, antiviral treatments, or as diagnostic probes is contemplated as part of the present invention. Exemplary uses as a diagnostic probe would include use of a conjugate of the present invention having hydrolytic cleavage activity for ribonucleic acid in determining the nucleotide sequence of the RNA, or may be used to detect polymorphisms in the RNA.

Incorporation of a texaphyrin metal complex catalyst at an internal position of an oligonucleotide is important for the generation of agents capable of exhibiting catalytic turnover since the conjugate must bind substrate with sufficient strength and specificity for specific cleavage to occur, yet, cleavage products must diffuse away from the conjugate catalyst or allow strand displacement in order for turnover to occur. Catalytic turnover is demonstrated herein using conjugates of the present invention.

The methods of the present invention are conducted under conditions sufficient to hydrolyze the RNA. Such conditions are known to those of skill in the art or can be determined by such persons without undue experimentation. It has been found that such conditions include physiologic conditions. This is especially useful when the texaphyrin complexes are used in vivo or ex vivo as a treatment procedure to hydrolyze RNA.

In the practice of the present invention, the texaphyrin macrocycle to be complexed to a metal ion may be chosen from any texaphyrin molecule, including those now known and disclosed in the U.S. patents and patent applications incorporated by reference herein. Representatives of texaphyrin metal complexes included within the present invention are encompassed within the following formula:

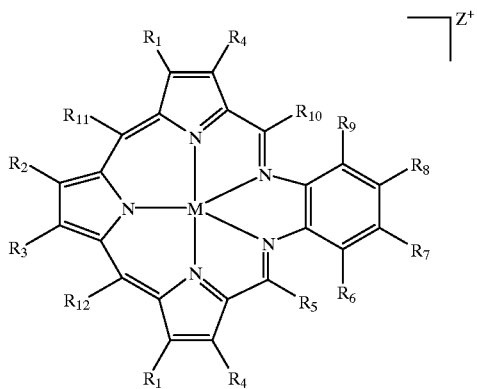

M is a divalent metal cation or a trivalent metal cation having catalytic activity for hydrolysis of ribonucleic acid. In particular, the metal is a lanthanide cation or a Lewis acidic cation such as Ce(III), Pr(III), Nd(III), Pm(III), Sm(III), Eu(III), Gd(III), Tb(III), Dy(III), Ho(III), Er(III), Tm(III), Yb(III), Lu(III), La(III), Sc(III), Y(III), In(III), Mn(III), Co(III), Ni(III), or Fe(III), for example. Divalent cations may be Ca(II), Mn(II), Co(II), Ni(II), Zn(II), Cd(II), Hg(II), Fe(II), Sm(II), or $UO_2$(II), for example. Preferred metal cations include Eu(III), Gd(III), Tb(III), or Dy(III).

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, an oligonucleotide, an oligonucleotide analog, a catalytic group, an antibody, a steroid, a hormone, a peptide having affinity for a biological receptor, a sapphyrin molecule, or a couple that is coupled to an oligonucleotide, an oligonucleotide analog, a catalytic group, an antibody, a steroid, a hormone, a peptide having affinity for a biological receptor, or a sapphyrin molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple that is coupled to a saccharide, an oligonucleotide, an oligonucleotide analog, a catalytic group, an antibody, a steroid, a hormone, a peptide having affinity for a biological receptor, or a sapphyrin molecule.

In the texaphyrin metal complexes of the conjugates of the present invention, at least one of $R_1$–$R_{12}$ is an oligonucleotide, oligonucleotide analog, or a couple that is coupled to an oligonucleotide or an oligonucleotide analog.

The charge, Z, is an integer value less than or equal to 5. In the context of the basic macrocycle with a divalent or trivalent cation, Z is 1 or 2. However, one skilled in the art in light of the present disclosure would realize that the charge Z would be altered so as to account for the choice of metal M, the pH under consideration, and charges present on any of substituents $R_1$–$R_{12}$ and charges present on any covalently bound molecule, for example charges of the phosphate groups on an oligonucleotide. For instance, if $R_1$=carboxyl and $R_2$–$R_{12}$=alkyl and the metal M=Tb$^{+3}$, and the solution is pH=7 (so that $R_1$=$CO_2^-$), the charge Z would be zero. The charge would be negative when substituents have a sufficient number of negative charges, for example, when a substituent is an oligonucleotide. The charge would be +5, for example, when the M is Dy$^{+}$ and the net charge of a substituent(s) is three positive charges.

It is understood by those skilled in the art that the complexes described in the present invention have one or more additional ligands providing charge neutralization and/or coordinative saturation to the metal ion. Such ligands include chloride, nitrate, acetate, cholate, and hydroxide, among others.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonene and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, and the term as used herein includes both unsubstituted aryls and aryls substituted with one or more nitro, carboxy, sulfonic acid, hydroxy, oxyalkyl or halide substituents. In this case, the substituent on the phenyl or naphthyl may be added in a synthetic step after the condensation step which forms the macrocycle.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$ alkyls being preferred, and diols of $C_{1-3}$ alkyls being more preferred; and polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. "Oxyalkyl" is meant to include polyethers with one or more functional groups. The number of repeating oxyalkyls within a substituent may be up to 200, preferably is from 1–20, and more preferably, is 1–10, and most preferably is 1–5. A preferred oxyalkyl is $O(CH_2CH_2O)_xCH_3$ where x=1–100, preferably 1–10, and more preferably, 1–5.

"Oxyhydroxyalkyl" means alkyl groups having ether or ester linkages, hydroxyl groups, substituted hydroxyl groups, carboxyl groups, substituted carboxyl groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5)_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary (CONHR) and tertiary (CONR'R") carboxyamides where each of R' and R" is a functional group as described herein.

Representative examples of useful amines include a primary, secondary or tertiary amine of an alkyl as described hereinabove.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether or the like.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol.

Sapphyrin compounds are disclosed in U.S. Pat. Nos. 5,041,078, 5,159,065, 5,120,411, 5,302,714, and 5,457,607; each patent is incorporated by reference herein.

Representative examples of useful steroids include any of the steroids of the following five categories: progestins (e.g. progesterone), glucocorticoids (e.g., cortisol), mineralocorticoids (e.g., aldosterone), androgens (e.g., testosterone) and estrogens (e.g., estradiol). The term "steroid" includes steroid derivatives. The term "hormone" includes hormones such as estradiol, histamine, or hormone mimics such as morphine.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

Hydrolytic cleavage of phosphate ester bonds of RNA texaphyrin complexes may be enhanced by additional catalytic groups appended to the texaphyrin complex or to a texaphyrin complex-oligonucleotide or -oligonucleotide analog conjugate. The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and texaphyrin metal complexes. The term "appended to the texaphyrin complex or conjugate" means that the catalytic groups are attached either directly to the texaphyrin metal complex or to the texaphyrin complex via a linker or couple of variable length, or are attached to an oligonucleotide or oligonucleotide analog portion of a conjugate either with or without a linker or couple of variable length.

Exemplary oligonucleotides or oligonucleotide analogs useful herein include, but are not limited to, polydeoxyribonucleotides, oligodeoxyribonucleotides, polyribonucleotide analogs, oligoribonucleotide analogs. It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates, phosphoramidates and the like. "Analog" as used herein also includes, but is not limited to, oligonucleotides having residues or linkers synthetically introduced therein, such as a ribonucleic acid residue within a DNA sequence, a branching linking agent such as a glycerol derivative, or an aminoalkyl linker, for example. Modification of the sugar, base, or phosphate portion of a residue is contemplated in the present invention.

Oligonucleotides have exquisite specificity for target sites and are easily designed. Oligonucleotides may be derivatized at the bases, the sugars, the ends of the chains, or at the phosphate groups of the backbone to promote in vivo stability. CpG sequences may be derivatized to minimize degradation; derivatization may be alkylation, and is preferably methylation. Modifications of the phosphate groups are preferred in one embodiment of the invention since phosphate linkages are sensitive to nuclease activity. Preferred derivatives are the methylphosphonates, phosphotriesters, phosphorothioates, and phosphoramidates. Derivatives may also contain alternating phosphorothioate and unmodified linkages, or alternating methylphosphonate and unmodified linkages, or alternating phosphorothioate and methylphosphonate linkages. Additionally, the phosphate linkages may be completely substituted with non-phosphate linkages such as amide linkages. Appendages to the ends of the oligonucleotide chains also provide exonuclease resistance. The 5' or 3' end may be derivatized or "capped" with a phosphoramidate linkage, an inverted nucleotide conjugated to the oligonucleotide via a 3'-3' linkage, an aminoacridine residue, or poly-L-lysine. Oligonucleotides may be designed to purposefully possess a mismatch in relation to a target RNA substrate, or to purposefully induce a loop or a bulge in a target RNA substrate. Methods for preparing texaphyrin-oligonucleotide conjugates modified for increased stabilization are known in the art and are disclosed in, for example, WO 94/29316, previously incorporated herein by reference.

Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy, propoxy, or methoxyethoxy. The alkenyl group is preferably allyl. The alkyl group is preferably a methyl group and the methyl group is attached to the 2' oxygen of the ribose. Other alkyl groups may be ethyl or propyl.

The term "internally-derivatized texaphyrin metal complex-oligonucleotide or -oligonucleotide analog conjugate" as used herein means that the texaphyrin metal complex is attached to the oligonucleotide or oligonucleotide analog via an internal linkage of the oligonucleotide or oligonucleotide analog. Not wanting to be bound by theory, the present inventors believe that hydrolysis is facilitated by the texaphyrin metal complex fitting across the minor groove of a duplex molecule. Therefore, any configuration of coupling groups between the texaphyrin metal complex and the oligonucleotide that would allow access to and across the minor groove is contemplated in the present invention. The length of a couple can readily be adjusted using the present phosphoramidite approach. When the texaphyrin is bound to a backbone linkage as in the present invention, a shorter couple results in fewer degrees of conformational freedom within the duplex with RNA, leading to more facile hydrolysis. Exemplary couples or coupling groups are amides, amine, disulfide, thioether, ether, polyether, ester, phosphate, or thiophosphate covalent bonds. In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond. Preferred couples include $O(CH_2)_nPO_4$ where n is 1–10; more preferably, n is 1–6; and most preferably, n is 3–6.

A conjugate may lack a base and/or a sugar, or may contain a derivatized base and/or sugar analog at or near the site of texaphyrin attachment. A nucleotide analog may be a carbocyclic nucleotide, for example. A conjugate may include a peptide nucleic acid.

In the practice of the present invention, at least one of $R_1$–$R_{12}$ is an oligonucleotide or oligonucleotide analog or a couple that is coupled to an oligonucleotide or an oligonucleotide analog. Also presently preferred are those compounds where $R_1$ is hydroxyalkyl or ethyl, and $R_2$, $R_3$, and $R_4$ are alkyl. Each of $R_7$ and $R_8$ may independently be hydrogen, hydroxyalkoxy, or oxyalkyl. Alternatively, $R_1$, $R_3$, $R_7$ or $R_8$ may be an oligonucleotide or oligonucleotide analog or a couple that is coupled to an oligonucleotide or an oligonucleotide analog.

In a preferred texaphyrin complex of the present invention, $R_1$, $R_2$, and $R_3$ are $CH_2CH_3$; $R_4$ is $CH_3$; $R_5$, $R_6$, $R_9$, $R_{10}$, $R_{11}$, and $R_{12}$ are H; $R_7$ is $OCH_3$, and $R_8$ is couple-oligonucleotide or couple-oligonucleotide analog. Alternatively, $R_7$ is an oligonucleotide or oligonucleotide analog or a couple that is coupled thereto, more preferably $O(CH_2)_nPO_4$-oligonucleotide where n is 1–8 and is preferably 3–6. Where $R_7$ is an oligonucleotide or oligonucleotide analog or a couple that is coupled thereto, $R_8$ may be H, $OCH_3$ or one of the previously listed preferred substituents. In a further preferred texaphyrin complex of the present invention $R_1$ is $(CH_2)_2CH_2OH$; $R_2$ and $R_3$ are $CH_2CH_3$; $R_4$ is $CH_3$; $R_5$, $R_6$, $R_9$, $R_{10}$, $R_{11}$, and $R_{12}$ are H; $R_7$ is $OCH_3$; and $R_8$ is couple-oligonucleotide or couple-oligonucleotide analog.

Water-soluble texaphyrins are often preferred for the applications described herein, particularly when in vivo administration and treatment is contemplated. "Water-soluble" means soluble in aqueous fluids to about 1 mM or better. Such characteristics allow these texaphyrins to be useful in a biological environment. Improved water solubility can be achieved by, for example, substituents chosen from saccharides or hydroxylated substituents.

In other presently preferred texaphyrin compounds, $R_1$–$R_{12}$ are as in Tables A and B for texaphyrins A1–A108; and M is as defined hereinabove. While the cited texaphyrins are presently preferred compounds for use in the present invention, the invention is not limited thereto and any texaphyrin complex that has activity as a hydrolyzing agent for RNA may be useful in the practice of the invention.

TABLE A

Representative Substituents for Texaphyrin Macrocycles A1–A108 of the Presnet Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | H |
| A2 | " | " | " | " | " | " |
| A3 | " | " | " | " | " | " |
| A4 | " | " | " | " | " | " |
| A5 | " | " | " | " | " | " |
| A6 | " | " | " | " | " | " |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | COOH | COOH | " | " | " |
| A13 | $CH_2(CH_2)_2OH$ | $COOCH_2CH_3$ | $COOCH_2CH_3$ | $CH_3$ | H | H |
| A14 | $CH_2CH_2CON(CH_2CH_2OH)_2$ | $CH_2CH_3$ | $CH_2CH_3$ | " | " | " |
| A15 | $CH_2CH_2ON(CH_3)CH_2$—$(CHOH)_4CH_2OH$ | " | " | " | " | " |
| A16 | $CH_2CH_3$ | " | " | " | " | " |
| A17 | $CH_2(CH_2)_2OH$ | " | " | " | " | " |
| A18 | " | " | " | " | " | " |
| A19 | " | " | " | " | " | " |
| A20 | $CH_2CH_3$ | $CH_3$ | $CH_2CH_2COOH$ | " | " | " |
| A21 | " | " | $CH_2CH_2CO$-oligonucleotide or analog thereof | " | " | " |
| A22 | $CH_2(CH_2)_2OH$ | $CH_2CH_3$ | $CH_2CH_3$ | " | " | " |
| A23 | " | " | " | " | " | " |
| A24 | " | " | " | " | " | " |
| A25 | " | " | " | " | " | " |
| A26 | " | " | " | " | " | " |
| A27 | " | COOH | COOH | " | " | " |
| A28 | " | $COOCH_2CH_3$ | $COOCH_2CH_3$ | " | " | " |
| A29 | $CH_2CH_2CO$-oligonucleotide or analog thereof | $CH_2CH_3$ | $CH_2CH_3$ | $CH_3$ | H | H |
| A30 | $CH_2CH_2CO$-oligonucleotide or analog thereof | " | " | " | " | " |
| A31 | $CH_2(CH_2)_2OH$ | " | $CH_2CH_2CO$-oligonucleotide or analog thereof | " | " | " |
| A32 | " | " | $CH_2CH_2CO$-oligonucleotide or analog thereof | " | " | " |
| A33 | $CH_2CH_3$ | $CH_3$ | $CH_2CH_2COOH$ | " | " | " |
| A34 | " | " | $CH_2CH_2CO$-oligonucleotide or analog thereof | " | " | " |
| A35 | $CH_2CH_3$ | $CH_2CH_3$ | $CH_2CH_3$ | " | " | " |
| A36 | " | " | " | " | " | " |
| A37 | " | " | " | " | " | " |
| A38 | " | " | " | " | " | " |
| A39 | $CH_2(CH_2)_2OH$ | $CH_2CH_3$ | $CH_2CH_3$ | $CH_3$ | H | COOH |
| A40 | " | " | " | " | " | COOH |
| A41 | " | " | " | " | " | CONHCH—$(CH_2OH)_2$ |
| A42 | " | " | " | " | " | CONHCH—$(CH_2OH)_2$ |
| A43 | " | " | " | " | " | CONHCH—$(CH_2OH)_2$ |
| A44 | " | " | " | " | " | H |
| A45 | " | " | " | " | " | $OCH_3$ |
| A46 | " | " | " | " | " | " |
| A47 | " | " | " | " | " | " |
| A48 | " | " | " | " | " | " |
| A49 | " | " | " | " | " | " |
| A50 | " | " | " | " | " | $CH_3$ |
| A51 | " | " | " | " | " | " |
| A52 | " | " | " | " | " | " |
| A53 | " | " | " | " | " | " |
| A54 | " | " | " | " | $CH_3$ | H |
| A55 | " | " | " | " | " | " |
| A56 | " | " | " | " | " | " |
| A57 | $CH_2(CH_2)_2OH$ | $CH_2CH_3$ | $CH_2CH_3$ | $CH_3$ | $CH_3$ | H |
| A58 | " | " | " | " | " | " |
| A59 | " | " | " | " | " | " |
| A60 | " | " | " | " | " | " |

TABLE A-continued

Representative Substituents for Texaphyrin Macrocycles A1–A108 of the Presnet Invention.
Substituents for R$_1$–R$_6$ are provided in TABLE A and for R$_7$–R$_{12}$ in TABLE B.

| TXP | R$_1$ | R$_2$ | R$_3$ | R$_4$ | R$_5$ | R$_6$ |
|---|---|---|---|---|---|---|
| A61 | " | " | " | " | " | " |
| A62 | " | " | " | " | " | " |
| A63 | " | " | " | " | " | H |
| A64 | " | " | " | " | " | F |
| A65 | " | " | " | " | CH$_2$(CH$_2$)$_6$OH | H |
| A66 | " | " | " | " | " | Br |
| A67 | " | " | " | " | " | NO$_2$ |
| A68 | " | " | " | " | " | COOH |
| A69 | " | " | " | " | " | CH$_3$ |
| A70 | " | " | " | " | C$_6$H$_5$ | H |
| A71 | " | COOH | COOH | " | CH$_2$CH$_3$ | " |
| A72 | " | COOCH$_2$CH$_3$ | COOCH$_2$CH$_3$ | " | CH$_3$ | " |
| A73 | CH$_2$CH$_2$CON(CH$_2$CH$_2$OH)$_2$ | CH$_2$CH$_3$ | CH$_2$CH$_3$ | " | " | " |
| A74 | CH$_2$CH$_2$ON(CH$_3$)CH$_2$(CHOH)$_4$CH$_2$OH | " | " | " | " | " |
| A75 | CH$_2$CH$_3$ | " | " | " | CH$_2$(CH$_2$)$_6$OH | " |
| A76 | CH$_2$(CH$_2$)$_2$OH | CH$_2$CH$_3$ | CH$_2$CH$_3$ | CH$_3$ | CH$_3$ or CH$_2$CH$_3$ | H |
| A77 | " | " | " | " | " | " |
| A78 | " | " | " | " | " | " |
| A79 | " | " | " | " | " | " |
| A80 | " | " | " | " | " | " |
| A81 | " | " | " | " | " | " |
| A82 | " | " | " | " | " | " |
| A83 | " | " | " | " | " | " |
| A84 | " | " | " | " | " | " |
| A85 | " | " | " | " | H | " |
| A86 | " | " | " | " | " | " |
| A87 | " | " | " | " | CH$_3$ or CH$_2$CH$_3$ | " |
| A88 | " | " | " | " | " | " |
| A89 | " | " | " | " | H | H |
| A90 | " | " | " | " | " | " |
| A91 | " | " | " | " | " | " |
| A92 | " | " | " | " | " | " |
| A93 | " | COOH | COOH | " | " | " |
| A94 | " | COOCH$_2$CH$_3$ | COOCH$_2$CH$_3$ | " | " | " |
| A95 | CH$_2$(CH$_2$)$_2$OH | CH$_2$CH$_3$ | CH$_2$CH$_2$CO-oligonucleotide or analog thereof | " | " | " |
| A96 | CH$_2$CH$_3$ | CH$_3$ | CH$_2$CH$_2$COOH | " | " | " |
| A97 | " | " | CH$_2$CH$_2$CO-oligonucleotide or analog thereof | " | " | " |
| A98 | CH$_2$(CH$_2$)$_2$OH | CH$_2$CH$_3$ | CH$_2$CH$_3$ | " | " | " |
| A99 | CH$_2$CH$_3$ | " | " | " | " | " |
| A100 | " | " | " | " | " | " |
| A101 | " | " | " | " | " | " |
| A102 | " | " | " | " | " | " |
| A103 | " | " | " | " | " | " |
| A104 | " | " | " | " | " | " |
| A105 | CH$_2$(CH$_2$)$_2$OH | " | " | " | " | " |
| A106 | " | " | " | " | " | " |
| A107 | " | " | " | " | " | " |
| A108 | " | " | " | " | " | " |

TABLE B

Representative Substituents for Texaphyrin Macrocycles A1–A108 of the Present Invention.
Substituents for R$_1$–R$_6$ are provided in TABLE A and for R$_7$–R$_{12}$ in TABLE B.

| TXP | R$_7$ | R$_8$ | R$_9$ | R$_{10}$ | R$_{11}$ | R$_{12}$ |
|---|---|---|---|---|---|---|
| A1 | O(CH$_2$)$_3$OH | O(CH$_2$)$_3$OH | H | H | H | H |
| A2 | O(CH$_2$CH$_2$O)$_3$CH$_3$ | O(CH$_2$CH$_2$O)$_3$CH$_3$ | " | " | " | " |
| A3 | O(CH$_2$)$_n$CON-linker-oligonucleotide or analog thereof, n = 1–10 | " | " | " | " | " |
| A4 | O(CH$_2$)$_n$CON-linker-oligonucleotide or analog thereof, n = 1–10 | H | " | " | " | " |
| A5 | OCH$_2$CO-oligonucleotide or analog thereof | " | " | " | " | " |

TABLE B-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A6 | $O(CH_2CH_2O)_3CH_3$ | " | " | " | " | " |
| A7 | $OCH_2CON$-linker-oligonucleotide or analog thereof | $O(CH_2CH_2O)_3CH_3$ | " | " | " | " |
| A8 | $OCH_2CO$-oligonucleotide or analog thereof | " | " | " | " | " |
| A9 | $O(CH_2CH_2O)_{100}CH_3$ | " | " | " | " | " |
| A10 | $OCH_2CON(CH_2CH_2OH)_2$ | H | " | " | " | " |
| A11 | $CH_2CON(CH_3)CH_2$—$(CHOH)_4CH_2OH$ | " | " | " | " | " |
| A12 | $CH_2CON(CH_3)CH_2$—$(CHOH)_4CH_2OH$ | " | " | " | " | " |
| A13 | $CH_2CON(CH_3)CH_2$—$(CHOH)_4CH_2OH$ | H | H | H | H | H |
| A14 | $CH_2CON(CH_3)CH_2$—$(CHOH)_4CH_2OH$ | " | " | " | " | " |
| A15 | $OCH_3$ | $OCH_3$ | " | " | " | " |
| A16 | $OCH_2CO_2$-oligonucleotide or analog thereof | H | " | " | " | " |
| A17 | $O(CH_2)_nCOOH$, n = 1–10 | " | " | " | " | " |
| A18 | $(CH_2)_n$—CON-linker-oligonucleotide or analog thereof, n = 1–10 | " | | | | |
| A19 | $YCOCH_2$-linker-oligonucleotide or analog thereof, Y = NH,O | " | " | " | " | " |
| A20 | $O(CH_2)_2CH_2OH$ | $O(CH_2)_2CH_2OH$ | " | " | " | " |
| A21 | " | " | " | " | " | " |
| A22 | $OCH_2COOH$ | $O(CH_2CH_2O)_3CH_3$ | " | " | " | " |
| A23 | $O(CH_2)_nCO$-oligonucleotide or analog thereof, n = 1–10 | H | " | " | " | " |
| A24 | $O(CH_2CH_2O)_3CH_3$ | $O(CH_2CH_2O)_n$-oligonucleotide or analog thereof, n = 1–10, in particular, n = 3 or 5 | " | " | " | " |
| A25 | $OCH_3$ | $OCH_2$-oligonucleotide or analog thereof | " | " | " | " |
| A26 | " | $CH_2CO$-oligonucleotide or analog thereof | " | " | " | " |
| A27 | " | $CH_2CO$-oligonucleotide or analog thereof | " | " | " | " |
| A28 | $OCH_3$ | $CH_2CO$-oligonucleotide or analog thereof | H | H | H | H |
| A29 | " | $OCH_3$ | " | " | " | " |
| A30 | " | — | " | " | " | " |
| A31 | H | $O(CH_2)_2COOH$, n = 1–10 | " | " | " | " |
| A32 | " | $(CH_2)_n$—CON-linker-oligonucleotide or analog thereof, n = 1–10 | " | " | " | " |
| A33 | $OCH_3$ | $O(CH_2CH_2O)_3$—$CH_3$ | " | " | " | " |
| A34 | " | " | " | " | " | " |
| A35 | H | $O(CH_2)_nCO$-oligonucleotide or analog thereof, n = 1–10 | " | " | " | " |
| A36 | $OCH_3$ | " | " | " | " | " |
| A37 | $O(CH_2CH_2O)_3CH_3$ | " | " | " | " | " |
| A38 | " | $O(CH_2CH_2O)_n$-oligonucleotide of analog thereof, n = 1–10 | " | " | " | " |
| A39 | $O(CH_2)_3OH$ | $O(CH_2)_3OH$ | $O(CH_2)_3OH$ | H | H | H |
| A40 | $O(CH_2CH_2O)_3CH_3$ | $O(CH_2CH_2O)_3CH_3$ | COOH | " | " | " |
| A41 | $O(CH_2CH_2O)_3CH_3$ | $O(CH_2CH_2O)_3CH_3$ | $(CH_2)_3OH$ | " | " | " |
| A42 | " | " | $O(CH_2CH_2O)_3CH_3$ | " | " | " |
| A43 | " | $O(CH_2)_3COOH$ | " | " | " | " |
| A44 | H | $OCH_2COOH$ | $OCH_3$ | " | " | " |
| A45 | " | $OCH_2COOH$ | " | " | " | " |
| A46 | " | $O(CH_2CH_2O)_3CH_3$ | " | " | " | " |
| A47 | $O(CH_2CH_2O)_3CH_3$ | " | " | " | " | " |
| A48 | " | $OCH_2CO$-oligonucleotide or analog thereof | " | " | " | " |
| A49 | " | $OCH_2COOH$ | " | " | " | " |
| A50 | " | $O(CH_2CH_2O)_3CH_3$ | $O(CH_2CH_2O)_3CH_3$ | " | " | " |
| A51 | " | $OCH_2COOH$ | " | " | " | " |
| A52 | $O(CH_2CH_2O)_3CH_3$ | $O(CH_2CH_2O)_{100}CH_3$ | $OCH_3$ | " | " | " |

TABLE B-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A53 | H | OCH$_2$CO-oligonucleotide or analog thereof | " | " | " | " |
| A54 | O(CH$_2$)$_3$OH | O(CH$_2$)$_3$OH | H | CH$_3$ | " | " |
| A55 | H | O(CH$_2$CH$_2$O)$_3$CH$_3$ | " | " | " | " |
| A56 | O(CH$_2$CH$_2$O)$_3$CH$_3$ | " | " | " | " | " |
| A57 | H | OCH$_2$CO-oligonucleotide or analog thereof | H | CH$_3$ | " | " |
| A58 | " | OCH$_2$CO-oligonucleotide or analog thereof | " | " | " | " |
| A59 | " | OCH$_2$CON(CH$_2$CH$_2$OH)$_2$ | " | " | " | " |
| A60 | O(CH$_2$CH$_2$O)$_3$CH$_3$ | O(CH$_2$CH$_2$O)$_{100}$CH$_3$ | " | " | " | " |
| A61 | " | OCH$_2$CO-olignucleotide or analog thereof | " | " | " | " |
| A62 | H | CH$_2$CON(CH$_2$)CH$_2$(CHOH)$_4$CH$_2$OH | " | " | " | " |
| A63 | O(CH$_2$CH$_2$O)$_3$CH$_3$ | O(CH$_2$CH$_2$O)$_3$CH$_3$ | OH | " | " | " |
| A64 | " | " | F | " | " | " |
| A65 | " | " | H | CH$_2$(CH$_2$)$_6$OH | " | " |
| A66 | " | " | Br | H | " | " |
| A67 | " | " | NO$_2$ | " | " | " |
| A68 | " | " | COOH | " | " | " |
| A69 | " | " | CH$_3$ | " | " | " |
| A70 | " | " | H | C$_6$H$_5$ | " | " |
| A71 | " | " | " | CH$_2$CH$_3$ | " | " |
| A72 | " | " | " | CH$_3$ | " | " |
| A73 | " | " | " | " | " | " |
| A74 | OCH$_3$ | OCH$_3$ | " | " | " | " |
| A75 | H | OCH$_2$CO-oligonucleotide or analog thereof | " | CH$_2$(CH$_2$)$_6$OH | " | " |
| A76 | O(CH$_2$)$_3$OH | O(CH$_2$)$_3$OH | H | CH$_3$ or CH$_2$CH$_3$ | CH$_3$ or CH$_2$CH$_3$ | CH$_3$ or CH$_2$CH$_3$ |
| A77 | O(CH$_2$CH$_2$O)$_3$CH$_3$ | O(CH$_2$CH$_2$O)$_3$CH$_3$ | " | " | " | " |
| A78 | O(CH$_2$)$_3$OH | O(CH$_2$CH$_2$O)$_3$CH$_3$ | " | " | " | " |
| A79 | H | O(CH$_2$)$_n$CO-oligonucleotide or analog thereof, n = 1,2,3 | " | " | " | " |
| A80 | H | O(CH$_2$)$_n$CO-oligonucleotide or analog thereof, n = 1,2,3 | " | " | " | " |
| A81 | H | O(CH$_2$)$_3$OH | " | " | " | " |
| A82 | O(CH$_2$)$_3$OH | O(CH$_2$)$_n$CO-oligonucleotide or analog thereof, n = 1,2,3 | " | " | " | " |
| A83 | O(CH$_2$CH$_2$O)$_3$CH$_3$ | O(CH$_2$)$_n$CO-oligonucleotide or analog thereof, n = 1–10 | " | " | " | " |
| A84 | " | O(CH$_2$)$_n$CO-oligonucleotide or analog thereof, n = 1,2,3 | " | " | " | " |
| A85 | " | O(CH$_2$CH$_2$O)$_3$CH$_3$ | " | " | " | " |
| A86 | " | " | " | " | CH$_2$(CH$_2$)$_2$OH | CH$_2$(CH$_2$)$_2$OH |
| A87 | " | " | " | CH$_3$ or CH$_2$CH$_3$ | " | " |
| A88 | " | O(CH$_2$CH$_2$O)$_3$CH$_3$ | " | " | " | " |
| A89 | O(CH$_2$CH$_2$O)$_3$CH$_2$—CH$_2$-oligonucleotide or analog thereof | O(CH$_2$CH$_2$O)$_{120}$CH$_3$ | H | H | H | H |
| A90 | H | oligonucleotide or analog thereof | " | " | " | " |
| A91 | OCH$_2$CO-oligonucleotide or analog thereof | OCH$_2$CO-oligonucleotide or analog thereof | " | " | " | " |
| A92 | CH$_2$CO-oligonucleotide or analog thereof | CH$_2$CO-oligonucleotide or analog thereof | " | " | " | " |
| A93 | " | " | " | " | " | " |
| A94 | " | " | " | " | " | " |
| A95 | H | YCOCH$_2$-linker-oligonucleotide or analog thereof | " | " | " | " |
| A96 | O(CH$_2$CH$_2$O)$_3$CH$_3$ | O(CH$_2$CH$_2$O)$_5$-oligonucleotide or analog thereof | " | " | " | " |
| A97 | " | O(CH$_2$CH$_2$O)$_5$-oligonucleotide or analog thereof | " | " | " | " |

TABLE B-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A98 | H | $O(CH_2)_3CO$-oligonucleotide or analog thereof | " | " | " | " |
| A99 | " | $O(CH_2)_3CO$-oligonucleotide or analog thereof | " | " | " | " |
| A100 | $OCH_3$ | " | " | " | " | " |
| A101 | $O(CH_2CH_2O)_3CH_3$ | " | " | " | " | " |
| A102 | " | $O(CH_2CH_2O)_n$-oligonucleotide or analog thereof, n = 1–10 | " | " | " | " |
| A103 | " | $O(CH_2CH_2O)_n$-oligonucleotide or analog thereof, n = 6 | " | " | " | " |
| A104 | " | $O(CH_2CH_2O)_n$-oligonucleotide or analog thereof, n = 3 | " | " | " | " |
| A105 | " | $O(CH_2CH_2O)_n$-oligonucleotide or analog thereof, n = 3 | " | " | " | " |
| A106 | $OCH_3$ | $O(CH_2CH_2O)_n$-oligonucleotide or analog thereof, n = 1–10 | " | " | " | " |
| A107 | H | $O(CH_2CH_2O)_n$-oligonucleotide or analog thereof, n = 1–10 | " | " | " | " |
| A108 | $O(CH_2CH_2O)_xCH_3$, x = 1–10 | $O(CH_2CH_2O)_n$-oligonucleotide or analog thereof, n = 1–10 | " | " | " | " |

One skilled in the art of organic synthesis in light of the present disclosure and the disclosures in the patents, applications and publications incorporated by reference herein could extend and refine the basic synthetic chemistry to produce texaphyrins having various substituents. For example, polyether-linked polyhydroxylated groups, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Phosphoramidites of a texaphyrin metal complex may be synthesized as set forth in U.S. Pat. No. 5,565,552, incorporated by reference herein. In the present methods, a texaphyrin metal complex having a free hydroxyl group was incubated under a nitrogen atmosphere with dichloromethane, diisopropylethylamine, 2-cyanoethyl tetraisopropylphosphorodiamidite, and 1H-tetrazole. After extraction and washing, the texaphyrin metal complex phosphoramidite is available for incorporation into standard solid-phase or solution-phase DNA synthesis schemes.

The present methods provide a means for attachment of a texaphyrin metal complex at an internal position within the sequence of an oligonucleotide or oligonucleotide analog. An oligonucleotide or oligonucleotide analog is synthesized by automated methods, selective deprotection of a hydroxyl group at an internal position is carried out, and coupling of this hydroxyl group with a texaphyrin metal complex phosphoramidite follows. Incorporation of a hydroxyl group into a deoxyribonucleotide molecule was accomplished using the following methods. A first method employed an abasic phosphoramidite reagent, termed an asymmetric branching phosphoramidite (Clontech Laboratories, Inc., Palo Alto, Calif.), that allowed the synthesis of a deoxyoligonucleotide analog containing a branch at an internal site. A second method used an RNA amidite monomer (e.g., adenosine (N-PAC) CED phosphoramidite, Biogenex, San Ramon, Calif. at an internal position.

The conjugate containing the branched residue was selectively deprotected post-synthetically using buffered hydrazine solution after capping the 5'-end with acetic anhydride. The conjugate containing the RNA monomer was selectively deprotected post-synthetically using buffered fluoride solution. In one method, the dimethoxytrityl protective group on the 5' end was left in place. In another method, the DMT group is removed and the hydroxyl group is capped with acetic anhydride. The free hydroxyl group was then coupled with the metallotexaphyrin phosphoramidite. An alternative approach for synthesizing the conjugate where the linkage is to the 2' position of a ribose is to deprotect the RNA residue immediately after coupling, attach the texaphyrin metal catalyst, and then resume DNA synthesis. A further alternative approach uses "inverted" RNA amidites (Biogenex, San Ramon, Calif., reagents that are protected so as to effect 5'-2' linked instead of 5'-3' linked RNA. A polystyrene column is preferred when using the RNA-linked approach. The above-described approaches to modifying an oligonucleotide at an internal position in the course of solid-phase synthesis are not heretofore described in the context of preparing texaphyrin metal complex oligonucleotide or -oligonucleotide analog conjugates. One of skill in this art in light of this disclosure would realize that more than one texaphyrin may be bound to an oligonucleotide having more than one internal linkage.

The oligonucleotide or oligonucleotide analog of the conjugates of the present invention are long enough to bind probably at least about 8 nucleotides of complementary nucleic acid. For catalysis of RNA cleavage where the conjugate is in excess compared to substrate, the oligonucleotide or oligonucleotide analog may have any length dictated by knowledge of the sequence of a substrate molecule. For catalysis of RNA cleavage where substrate is in excess, the oligonucleotide or oligonucleotide analog must bind substrate so as to effect catalysis and must also be designed so that the cleaved products do not bind the conjugate so tightly that they prevent strand displacement or do not diffuse away. The present inventors demonstrate herein turnover using a conjugate having 7 bases on one side and 15 bases on the other side of the point of metallotexaphyrin attachment. It is possible that an RNA substrate molecule is able to displace the reaction product bound to the longer side of the conjugate. One of skill in this art in light of this disclosure would be able to design oligonucleotides and oligonucleotide analogs that would have sufficiently low melting temperatures to allow cleaved products to diffuse away from the catalytic conjugate or to allow substrate RNA strand invasion. It is well known that A-T bonds are less strong than G-C bonds, having two hydrogen bonds rather than three hydrogen bonds. Therefore, a conjugate having a sequence of nucleotides rich in A and T residues may be longer than one having a sequence of nucleotides rich in G and C residues, and still allow diffusion of product away from the reaction site to allow for turnover of the catalyst.

The use of texaphyrin complexes to hydrolyze RNA in vivo as a treatment procedure relies on the effective localization of the complex to the site of desired cleavage. A site of desired cleavage may be a position novel to undesired organisms in terms of health care. A site of desired cleavage may be an RNA encoding a product deleterious to the host or may be a normal RNA that is deleterious in some way. Treating native RNA with a texaphyrin metal complex-oligonucleotide or -oligonucleotide analog conjugate results in the conjugate binding to a complementary RNA sequence via the appended oligonucleotide or analog thereof. The texaphyrin complex then cleaves the RNA proximal to this specific site. Further, the binding of a conjugate to a DNA-RNA double helix will form a triple helix which has sufficient stability for effective cleavage to occur. Cleavage occurs most efficiently when the internally-derivatized conjugate and the target substrate are not exactly complementary, i.e., an area of "local melting" is present. By "local melting" is meant a loop or bulge, an abasic site, or a mismatched base(s), for example. The examples provided herein demonstrate cleavage with a variety of mismatched duplexes in relation to the texaphyrin metal complex attachment site; a mismatch or loop near a site of texaphyrin metal complex attachment provides optimal cleavage.

The texaphyrin metal complex-oligonucleotide or -oligonucleotide analog conjugates may be useful for inhibiting the expression of a gene in an animal or in a particular tissue of an animal by targeted intracellular mRNA hydrolysis. The conjugates and present methods of hydrolysis would have immediate applications for anti-viral and anti-bacterial therapy as well as cancers (an oligonucleotide, or analog thereof, complementary to an oncogene, for example) and inflammatory responses that are caused by the overexpression of certain proteins.

An exemplary method for delivering texaphyrin metal complex-oligonucleotide or -oligonucleotide analog conjugates into a cell is the use of texaphyrin-oligonucleotide-glycoconjugates for carrying oligonucleotides specific for targeted sequences. Conjugates linked through a disulfide bridge to a glycoconjugate could be significantly more effective in reaching a target site than the corresponding oligonucleotide. Poly-L-lysine can be substituted by three components: an oligonucleotide as a recognition signal, a therapeutic texaphyrin-metal complex, and gluconoic acid as a neutralizing and solubilizing agent. This type of neutral, highly water-soluble glycosylated polymer may be an efficient carrier to deliver drugs into cells.

Texaphyrin-oligonucleotide conjugates are taken up by eukaryotic cells as observed by fluorescent localization and reported in PCT publications WO 96/40253 and WO 96/38461. HL-60 cells (human promyelocytic leukemia cell line) were incubated with a solution (5 $\mu$M final conc.) of a texaphyrin-oligonucleotide conjugate complexed with either a Y(III) metal ion or a Lu(III) metal ion (where the oligonucleotide is a phosphorothioate with 15 bases). The cells were incubated for a minimum of 10 min and up to about 60 min, after which the cells were washed. Fluorescence was measured with a confocal argon laser, which excites at 488 nm. To view the fluorescence created by the texaphyrin, a cut-off filter was used to eliminate wavelengths below 700 nm. The resulting fluorescence images showed diffuse cytoplasmic fluorescence with some evidence of local "hot spots" of concentrated fluorescence. That texaphyrin-oligonucleotide conjugates can be effective and specific antisense agents, i.e., that they are able to enter a cell, locate the intended substrate RNA, and cleave the intended substrate RNA is demonstrated by studies carried out using 5' DyTx-anti-c-myc constructs for in vitro oncogene suppression in HL-60 cells. 5'-Derivatized DyTx oligonucleotide conjugates having phosphorothioate residues and having a sequence complementary to a c-myc splice site were added to HL-60 cells, and cell proliferation was assayed using the standard MTT assay. The antisense conjugate exhibited growth inhibition above background levels. The same conjugate substituted with a metal known not to have hydrolytic activity for RNA had no inhibitory activity for cell proliferation.

For the above-described uses, texaphyrin metal complex-oligonucleotide or -oligonucleotide analog conjugates are provided as pharmaceutical preparations. A pharmaceutical preparation of a conjugate may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a conjugate of the present invention and the pharmaceutically acceptable carriers are then easily administered in a variety of dosage forms. Administration may be intravenous, intraperitoneal, parenteral, intramuscular, subcutaneous, oral, or topical, with topical and intravenous administration being preferred, and intravenous being more preferred.

Solutions of the conjugates in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Topical creams, emulsions, solutions, and the like are contemplated for applications to surface areas of the body. Topical application may also be by iontophoresis.

Excipients and preservatives that preserve oligonucleotide stability are chosen. The highly negatively charged phosphate or sulfur groups of the backbone of the oligonucleotide may be irritating to epithelial or other surface cells. Counterions may be used for formulation purposes to prevent irritation.

Pharmaceutical forms include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A reliable assay for RNA hydrolysis is an assay for hydrolysis of a complementary ribonucleic acid as described in present Examples 3 and 4. Cleavage by a conjugate would demonstrate that the conjugate has the intended potency and activity. To assay the level of hydrolytic activity, and also for characterization purposes, the conjugates of the present invention were examined for site-specific hydrolysis of complementary or nearly complementary RNA substrates under first-order conditions, i.e., where the conjugate is present in excess of the concentration of substrate RNA. For determination of catalytic turnover, an assay under second-order reaction conditions where the concentration of substrate exceeds that of the conjugate catalyst and where cleavage in excess of the concentration of conjugate catalyst is observed is evidence of catalytic turnover.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

An RNA Amidite Method for Coupling Texaphyrin Internally in an Oligonucleotide

The present example provides for the preparation of a texaphyrin-oligonucleotide conjugate where the texaphyrin is bound to an internal nucleotide; the method uses an RNA amidite as a starting material. A dysprosium texaphyrin phosphoramidite was coupled to the free 2' hydroxyl group of an RNA residue positioned within a deoxynucleotide having standard 5'-3' linkages. A dysprosium texaphyrin phosphoramidite and methods of making are provided herein. An earlier method of preparing such an amidite is described in U.S. Pat. No. 5,565,552, incorporated by reference herein. The texaphyrin used herein had R groups as follows: $R_1$, $R_2$, $R_3$ are $CH_2CH_3$; $R_4$ is $CH_3$; $R_5$, $R_6$ and $R_9$–$R_{12}$ are H; $R_7$ is $OCH_3$; and $R_8$ is -linker where the linker was either $O(CH_2)_3PO_4$ or $O(CH_2)_6PO_4$ ($DyTxO(CH_2)_nPO_4$ where n is 3 or 6).

A texaphyrin phosphoramidite compound for use in coupling internally in an oligonucleotide where the linker was $O(CH_2)_6PO_4$ was prepared as follows. A further compound having the linker $O(CH_2)_3PO_4$ was prepared in a similar manner substituting a trimethylene compound for the hexyl compound described below. One of skill in this art would be able to synthesize other texaphyrin phosphoramidite compounds where n is 1–10 in light of the present disclosure.

1,2-Dinitro-4-hydroxy-5-methoxybenzene. Dinitroveratrole (5 g, 0.0219 mol) was dissolved in glacial acetic acid (50 mL), and concentrated HBr (48% w/w in water, 165 mL) was added all at once at room temperature (RT). The reaction temperature was elevated to 110° C., and the system was stirred for 6 h. After cooling to RT, ice water (150 mL) was added and a mixture of starting material and target was extracted from the aqueous phase using chloroform (2×400 mL). Target material was extracted from the chloroform layer using 2N sodium hydroxide solution (600 mL). The basic aqueous phase was washed with chloroform (2×200 mL) to remove remaining traces of starting material. The organic layers from the basic extractions were combined and dried over anhydrous magnesium sulfate. Removal of solvents under reduced pressure resulted in recovered starting material as a bright crystalline solid (2.35 g). The basic aqueous extract was acidified to pH<1 using conc. HCl (37 mL) and extracted with ethyl acetate (2×250 mL). The organic extracts were combined and dried over anhydrous magnesium sulfate. Solvents were removed under reduced pressure to yield the title compound as a yellow, powdery solid (1.82 g).

1,2-Dinitro-4-(1-hydroxyhexyl) oxy-5-methoxybenzene. To a solution of the methoxybenzene prepared above (270 mg, 1.259 mmol) in acetonitrile (40 mL) was added 6-bromo-1-hexanol (330 mL, 2.519 mmol), followed by sodium iodide (190 mg, 1.259 mmol) and potassium carbonate (697 mg, 5.045 mmol). The reaction was heated at 70° C. under a nitrogen atmosphere. After 5 days, the reaction mixture was cooled to 0° C. and filtered through a fine sintered glass funnel. Solvents were removed under reduced pressure and the resulting solid was dissolved in isopropyl alcohol (2 mL). The target product was precipitated by the addition of hexane (20 mL) to the rapidly stirred solution. The solid was filtered, washed with hexane and dried under reduced pressure to yield the crude target as a bright yellow solid (344 mg). Purification by short-bed silica gel chromatography using methylene chloride as the mobile phase resulted in the isolation of the product as a pale yellow crystalline solid (274 mg, 69%).

4-(1-Hydroxyhexyl) oxy-5-methoxy-1,2-phenylenediamine. 1,2-Dinitro-4-(1-hydroxyhexyl) oxy-5-methoxybenzene (300 mg, 0.9546 mmol) was dissolved in methanol (30 mL). Conc. HCl (1 mL) was added, followed by palladium catalyst (10% on activated carbon, 90 mg). The reaction was shaken under a hydrogen atmosphere at 45 psi. After 5 h, when the uptake of hydrogen was complete, the catalyst was removed by filtration over celite. Solvent was removed under reduced pressure to yield the target compound as the dihydrochloride salt (305 mg, 98%).

4,5,9,24-Tetraethyl-16(1-hydroxyhexyl)oxy-17-methoxy-pentaazapentacyclo[20.2.1.1$^{3,6}$.1$^{8,11}$.0$^{14,19}$]heptacosa-1,3,5,7,9,11(27),12,14,16,18,20,22(25),23-tridecaene. To a solution of the above phenylenediamine.2HCl (485 mg, 1.4821 mmol) in methanol (240 mL) was added solid 2,5-bis[5-formyl-3-ethyl-4-methylpyrrol-2-yl)methyl]-3,4-diethylpyrrole in one go, under a nitrogen atmosphere. After heating at 75° C. for 2 h, the reaction was allowed to cool to RT. Charcoal (330 mg) was added to the solution and the system was stirred for 15 min. The charcoal was removed by filtration over celite, and the solvent was removed under reduced pressure. The target compound was isolated as the dihydrochloride salt in the form of an orange glass (900 mg, 85%).

Dysprosium complex of 4,5,9,24-tetraethyl-16 (1-hydroxyhexyl) oxy-17-methoxy-pentaazapentacyclo [20.2.1.1$^{3,6}$.1$^{8,11}$.0$^{14,19}$]heptacosa-1,3,5,7,9,11(27),12,14,16,18,20,22(25),23-tridecaene, cpd. $1_A$. To a solution of the tridecaene prepared above (130 mg, 0.1824 mmol) in methanol (30 mL) was added dysprosium nitrate pentahydrate (120 mg, 0.2736 mmol), followed by triethylamine (260 mL, 1.834 mmol). The reaction was heated under gentle reflux open to the air. After 2.5 h, the reaction was allowed to cool to RT and was filtered through a pad of celite. Solvent was removed under reduced pressure and the resulting crude complex was triturated in acetone (30 mL) for 10 min. The solid was isolated by suction filtration and dried under reduced pressure. To remove unbound dysprosium metal ion, the complex was dissolved in a mixture of methanol/water (9:1, 15 mL) and gently agitated with zeolite (SAY-54, 600 mg), which had been previously rinsed with dilute HCl and deionized water. After 1.5 h, the zeolite was removed by filtration and the process was repeated using fresh zeolite. After removal of the zeolite, n-butyl alcohol (10 mL) was added to the system to prevent bumping during solvent removal. Solvents were removed under reduced pressure to yield the target compound $1_A$ as the dinitrate salt in the form of a deep green solid (97 mg, 58%). MS (FABLR) M—HNO$_3$—NO$_3$-796.

Dysprosium complex of 2-cyanoethyl-N,N-diisopropyl-6-(4,5,9,24-tetraethyl-17-methoxy-pentaazapentacyclo [20.2.1.1$^{3,6}$.1$^{8,11}$.0$^{14,19}$]-heptacosa-1,3,5,7,9,11(27), 12,14,16,18,20,22(25),23-tridecaene-16(1-oxy) hexylphosphoramidite, cpd. $1_B$. To the solid DyTx complex prepared above (230 mg, 0.250 mmol) under a strict nitrogen atmosphere was added anhydrous dichloromethane (22 mL) followed by 2-cyanoethyl tetraisopropylphosphorodiamidite (793 mL, 2.496 mmol), N,N-diisopropylethylamine (131 mL, 0.749 mmol), and 1H-tetrazole (35 mg, 0.500 mmol). After 4 h, the reaction was washed with saturated sodium bicarbonate (15 mL), followed by saturated sodium chloride (15 mL). The organic layer was dried over anhydrous magnesium sulfate for 5 min, concentrated to a volume of 2.9 mL, and then added dropwise to vigorously stirring diethyl ether (153 mL). The resulting solid was filtered using a fine sintered glass fritted funnel and dried under high vacuum to yield the title compound $1_B$ as a deep green solid (142 mg).

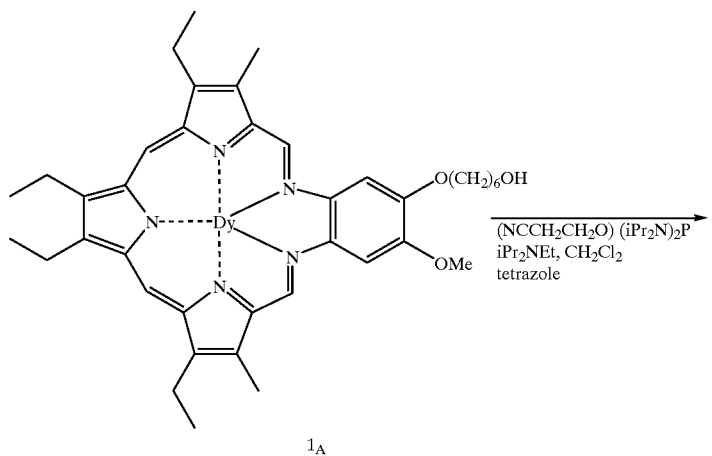

$1_A$

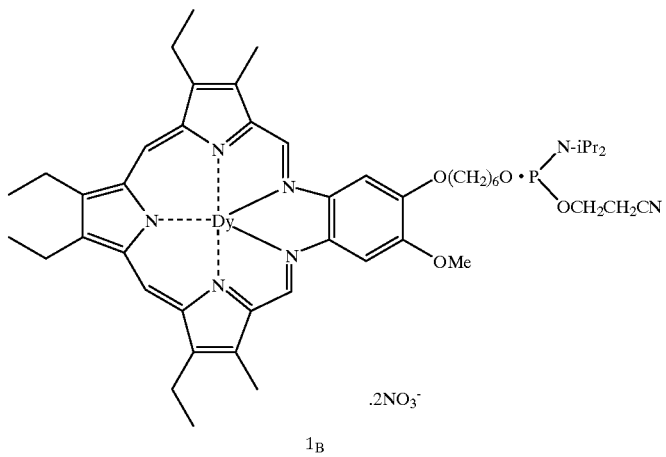

1B

A DNA oligomer having nine nucleotides was prepared on a 1 μmol scale using a standard protocol for a DNA synthesizer as provided by the manufacturer (Model 392, Perkin-Elmer, Foster City, Calif.). An adenosine residue was coupled to the growing chain using an adenosine RNA amidite (adenosine (N-PAC) CED phosphoramidite; BioGenex, San Ramon, Calif.). DNA synthesis was continued for an additional eight cycles using standard bases to give a sequence of 18 residues. The final 5'-DMT protective group was left intact.

The solid-support column containing the 18-residue oligonucleotide was removed from the synthesizer, attached to two disposable syringes (3 mL), and treated with a 1:1 solution of tetrabutylammonium fluoride (1M in THF, Aldrich, Milwaukee, Wis.) and 2M triethylammonium acetate buffer (Glen Research, Sterling, Va.), ca. 2 1 mL, for 1.5 h by periodically pushing reagent through the column with the syringes. This process was repeated using fresh syringes with a 2:1 solution of tetrabutylammonium fluoride (1M in THF, Aldrich, Milwaukee, Wis.) and 2M triethylammonium acetate buffer (Glen Research) for 1 h. The column was then washed with ca. 20 mL acetonitrile and placed back on the synthesizer.

The column was then treated with the DyTx amidite using an RNA coupling cycle as provided by the manufacturer of the DNA synthesizer and modified as follows; the initial DMT removal step was omitted; the support was coupled with the DyTx amidite three times for 10 min; and the standard oxidation, capping, and DMT removal steps were allowed to proceed as usual.

The resulting support-bound DyTx-oligonucleotide conjugate was removed from the solid support and deprotected by treatment with ammonium hydroxide (conc.): aqueous methylamine solution (40% aqueous, Aldrich, Milwaukee, Wis.) for 90 min at ambient temperature. An important aspect of this deprotection method is the use of acetyl-protected cytidine amidites during synthesis (Glen Research). Crude DyTx-oligonucleotide conjugate was purified by ethanol precipitation, reverse-phase HPLC, and gel electrophoresis.

Exemplary texaphyrin oligonucleotide conjugates prepared by the RNA amidite method are as follows. The bond between the linking phosphate group and the "A" residue is a 2' linkage.

```
5'-TGG AGA CTA CAT CTG TGA -3'      SEQ ID NO: 1
             |
   DyTx-O(CH₂)₆-PO₄

5'-TGG AGA CTT AAT CTG TGA -3'      SEQ ID NO: 2
             |
   DyTx-O(CH₂)₆-PO₄

5'-TGG AGA CTA CAT CTG TGA -3'      SEQ ID NO: 1
             |
   DyTx-O(CH₂)₃-PO₄

5'-TGG AGA CTT AAT CTG TGA -3'      SEQ ID NO: 2
             |
   DyTx-O(CH₂)₃-PO₄
```

Further texaphyrin oligonucleotide conjugates where the texaphyrin is bound in a 2' linkage were prepared using guanosine, cytosine, or uridine ribonucleotides analogous to the adenosine 2' conjugates of the present example. A control oligonucleotide was also synthesized having an adenosine RNA residue at position 10 of an 18-nucleotide molecule; the adenosine residue had a silyl protective group at the 2'-O position.

This method of using an RNA phosphoramidite to construct an oligonucleotide conjugate internally-derivatized with texaphyrin provides an additional (negatively charged) phosphate group near the site of attachment.

This type of conjugate is stereoisomerically pure. The RNA amidite-derived conjugates are conformationally rigid with the bond to the 2'-hydroxyl position on the ribose moiety directing the linkage towards the minor groove of a RNA/DNA heteroduplex. Not wanting to be bound by theory, it is thought by the present inventors that hydrolysis occurs more efficiently across the minor groove since the RNA is more easily accessed across the minor groove of the RNA/DNA heteroduplex.

EXAMPLE 2

An Asymmetric Branching Amidite Method for Coupling Texaphyrin Internally in an Oligonucleotide The present example provides a further method for the preparation of a texaphyrin-oligonucleotide conjugate where the texaphyrin is bound by an internal linkage; the method uses an asymmetric branching phosphoramidite as a starting material. A dysprosium texaphyrin phosphoramidite was prepared as described in Example 1.

A DNA oligonucleotide of 18 residues was prepared at a 1 μmol scale, with an asymmetric branching amidite (Clontech Laboratories, Inc., Palo Alto, Calif. programmed to be coupled as the 10th residue within the sequence. The coupling time was manually extended to 10 min for this amidite. The synthesis was performed "DMT Off", and the 5'-hydroxyl group was capped with acetic anhydride for 2×60 sec using manual control of the synthesizer. The synthesis column was removed from the synthesizer, and the levulinyl group selectively removed following the manufacturer's protocol (treatment for 15 min with 0.5 M hydrazine solution in 3:2 pyridine:acetic acid). The column was placed back on the synthesizer and coupled with DyTx phosphoramidite, deprotected, and purified as outlined in Example 1.

Exemplary derivatives prepared by the asymmetric branching method are as follows.

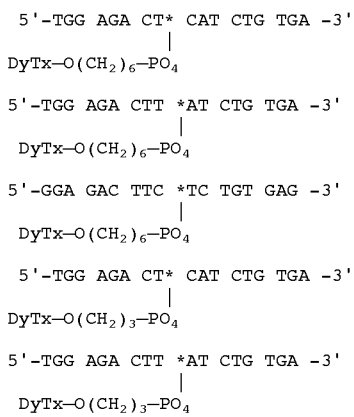

*designates the asymmetric branching linkage:

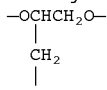

A control oligonucleotide lacking DyTx was also synthesized having an asymmetric branching residue at position 10 of an 18 residue molecule. One of skill in the art, in light of the present disclosure, would understand that a C in an asymmetric branching linker of the present disclosure means a carbon atom, whereas a C in an oligonucleotide means a cytosine DNA or RNA residue.

Oligonucleotides having an asymmetric branching amidite contain a diastereomeric position within the linker and, thus, are a mixture of two isomers. Solution-phase derived conjugates, such as conjugates prepared using UNI-LINK™ AminoModifier, and AminoModifier II (Clontech, Palo Alto, Calif., are also contemplated in the present invention, and would also contain a mixture of diastereomers.

EXAMPLE 3

RNA Hydrolysis Using a Conjugate where Texaphyrin is Coupled Internally in an Oligonucleotide The present example provides results of studies carried out on hydrolysis of RNA using a texaphyrin-oligonucleotide conjugate where the oligonucleotide is complementary DNA or near-complementary DNA and where the texaphyrin is coupled internally to the oligonucleotide.

An RNA having 36 residues (3'-A AAU AAA ACC UCU GAG GUA GAC ACU CGG CCC ACA AC -5', SEQ ID NO: 3) labeled with $^{32}$P at the 5'-end (ca. 70,000 cpm) was added to Eppendorf-type microfuge tubes containing 4×hydrolysis buffer and control oligonucleotide or conjugate test species to give a solution of final concentrations as follows: NaCl, 100 mM; EDTA, 25 μM; HEPES buffer, pH 7.5, 50 mM; oligonucleotide conjugate test species, 100 nM; RNA oligomer, ca. 2 nM. Samples which contained DNA controls (i.e., oligonucleotide starting materials which lack the DyTx complex, obtained during HPLC purification of the conjugate) also contained free DyTx complex, 100 nM final concentration. Samples were vortexed, centrifuged briefly, and incubated in the absence of light at 37° C. for 15 h. The samples were precipitated using standard techniques, resuspended in gel loading buffer, and subjected to electrophoresis on a 20% denaturing polyacrylamide gel.

An autoradiograph of the gel showed that hydrolytic cleavage of the RNA substrate occurred only in those samples containing conjugates. By comparison with sequencing lanes, hydrolysis occurred at substrate sites adjacent to the attachment site of the DyTx upon formation of a duplex between the conjugate and RNA substrate. Further, conjugates that contained a non-complementary base next to the site of DyTx attachment displayed ca. 10-fold less hydrolysis at that non-complementary site. Control lanes containing DNA having an abasic site at a position corresponding to the position of attachment of texaphyrin in an experimental conjugate and free DyTx complex showed no hydrolysis above background.

Results of hydrolysis of RNA by conjugates internally modified with DyTx are as follows. The arrow (↓) indicates preferred sites of observed cleavage, while the arrowhead (v) indicates cleavage at about a 10-fold lower extent. The asterisk (*) indicates the asymmetric branching linking site. Mismatched base pairs and unmatched bases are in bold.

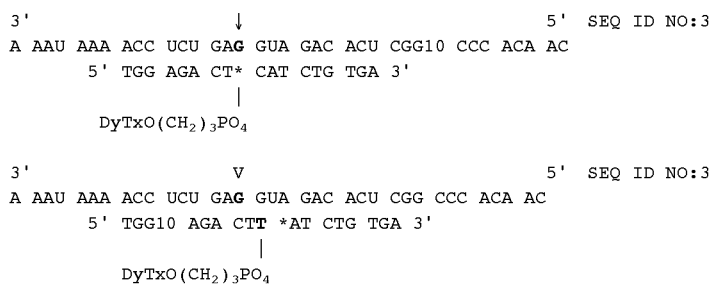

-continued

```
3'                    ↓                      5'    SEQ ID NO:3
A AAU AAA ACC UCU GAG GUA GAC ACU CGG CCC ACA AC
        5' TGG AGA CTA CAT CTG TGA 3'
                     |
            DyTxO(CH₂)₃PO₄

3'                    v                      5'    SEQ ID NO:3
A AAU AAA ACC UCU GAG GUA GAC ACU CGG CCC ACA AC
        5' TGG AGA CTT AAT CTG TGA 3'
                     |
            DyTxO(CH₂)₃PO₄

3'                  v↓                       5'    SEQ ID NO:4
A AAU AAA ACC UCU GAA GUA GAC ACU CGG CCC ACA AC
        5' TGG AGA CT* CAT CTG TGA 3'
                     |
            DyTxO(CH₂)₃PO₄

3'                    ↓                      5'    SEQ ID NO:4
A AAU AAA ACC UCU GAA GUA GAC ACU CGG CCC ACA AC
        5' TGG AGA CTT *AT CTG TGA 3'
                     |
            DyTxO(CH₂)₃PO₄

3'                    ↓                      5'    SEQ ID NO:4
AA AUA AAA CCU CUG AAG UAG ACA CUC GGC CCA CAA C
        5' GGA GAC TTC *TC TGT GAG 3'
                     |
            DyTxO(CH₂)₃PO₄
```

*designates the asymmetric branching linkage: —OCHCH₂O—
                                                |
                                               CH₂
                                                |

These results confirm that the DyTx is attached at an internal position within the conjugate. The results also show that DyTx was able to hydrolyze the RNA at regions adjacent to this point of attachment within the hybridized complex, i.e., within a predominantly duplex region. Furthermore, the cleavage is sequence-specific as evidenced by the specificity of the observed cleavage sites and by the decreased activity of the additional mismatch. Conjugates where the texaphyrin had a three carbon linker and those having a six carbon linker both accomplished hydrolysis of the RNA substrate. Conjugates having a "G", "C", or a "U" ribonucleotide residue at the point of texaphyrin attachment also demonstrated cleavage, especially when the ribonucleotide was mismatched with its base pair.

The asymmetric branching agent does not contain a DNA base or sugar and, thus, hybrids of an oligonucleotide conjugate containing an asymmetric branching agent with an RNA substrate contain a non-base-paired region that may enhance hydrolysis by the texaphyrin metal complex. An oligonucleotide conjugate where a texaphyrin is bound to an adenosine residue as in Example 1 may be designed to have the adenosine opposite or adjacent to a non-complementary base of a target substrate. This region of base-mismatch within the RNA-DNA duplex may enhance hydrolysis compared to hydrolysis at base-paired duplex regions. These observations are substantiated by the hydrolysis experiments since use of internally-derivatized DyTx conjugates having a mismatch at the site of attachment caused site-specific hydrolysis of the RNA at regions adjacent to the position of the texaphyrin. An additional mismatch results in less hydrolytic cleavage at that mismatched site possibly due to less efficient hybridization.

The levels of RNA hydrolysis observed using internally-derivatized conjugates were similar to those obtained using 5' derivatized conjugates (WO 94/29316). Changing the site of texaphyrin derivatization to an internal position within the oligonucleotide caused the site of hydrolysis to correspondingly change.

EXAMPLE 4

Demonstration of Catalytic Turnover

The present example provides results from studies of the RNA hydrolysis properties of an oligodeoxynucleotide internally-derivatized with dysprosium(III) texaphyrin (DyTx), compound 1. The texaphyrin had R groups as described in Example 1. The symbol (*) indicates the asymmetric branching linkage:

```
    —OCHCH₂O—
        |
       CH₂
        |
    5' TGGAGACT*CATCTGTGA 3'                    1
                |
          DyTxO(CH₂)₃PO₄
```

For comparison, a deoxynucleotide having twenty residues derivatized at the 5'-hydroxyl position using the same DyTx catalyst, compound 2, was also studied.

5'-DyTx—O(CH₂)₃PO₄—CATCTGTGAGCCGGGTGTTG-3'    2

(SEQ ID NO:5)

Site-specific hydrolysis of a complementary RNA substrate 3 using each of the DyTx-DNA conjugates 1 and 2 was examined under two differing conditions: i) where the DyTx-DNA conjugate was present in ca. 10-fold excess concentration relative to the RNA substrate (pseudo-first-order conditions); and ii) where the RNA substrate was present in ca. 10-fold excess concentration relative to the DyTx-DNA conjugate (second-order conditions).

```
              3'
    AAAUAAAACCUCUGAAGUAGACACUCGGCCCACAAC 5'          3

(SEQ ID NO:4)
```

Figure 2A:
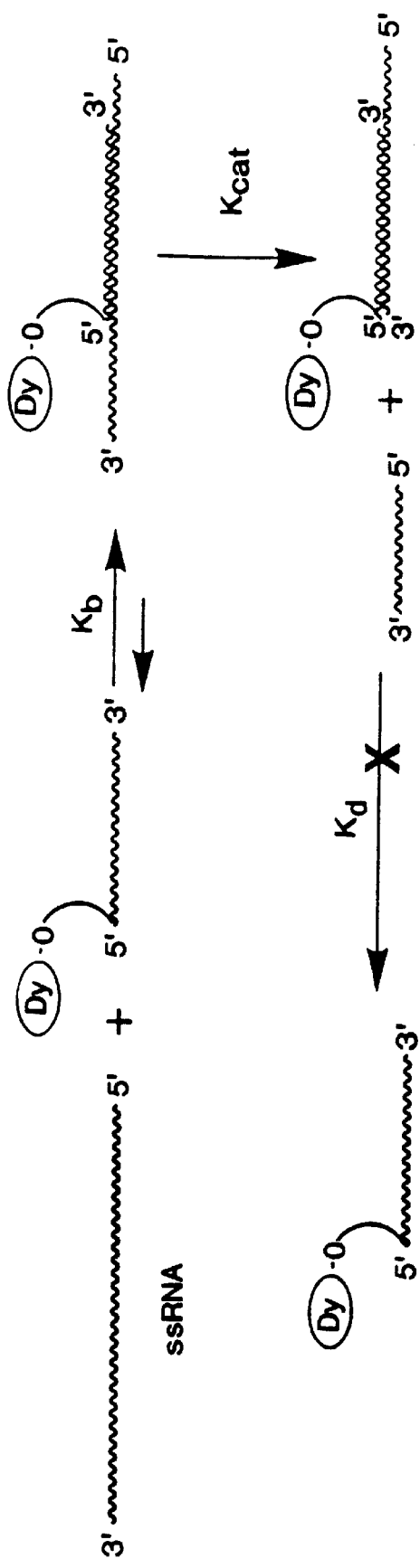
FIGS. 2A and 2B provide possible mechanisms for the differing hydrolytic action of an oligonucleotide end-derivatized with a dysprosium texaphyrin (FIG. 2A) and an oligonucleotide internally-derivatized with a dysprosium texaphyrin (FIG. 2B).
Figure 2B:
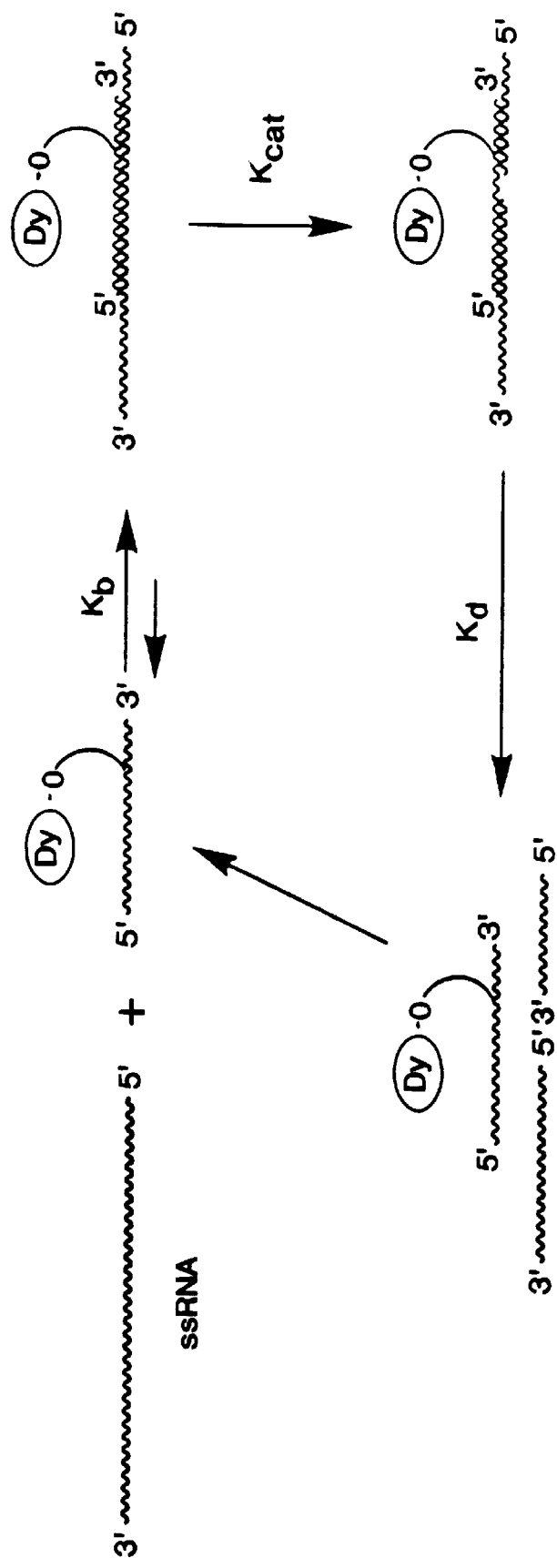

Buffered solutions were prepared of each conjugate (25 nM DyTx-DNA conjugate, 50 mM HEPES, pH 7.5, 100 mM NaCl, 25 μM EDTA, 2 units/uL RNasin™ nuclease inhibitor (Promega Corporation, Madison, Wis.), and 2 mM dithiothreitol, all concentrations are final). To assay under conditions having conjugate excess, 5'-$^{32}$P-radiolabeled substrate RNA (ca. 2 nM) was incubated for 5 min at 60° C., then added to the conjugate solutions. To assay under conditions having substrate excess, 5'-$^{32}$P-radiolabeled substrate RNA (ca. 2 nM) and unlabeled RNA (250 nM were mixed and incubated together for 5 min at 60° C., then added to the conjugate solutions. The resulting mixtures were each ($K_b$) and hydrolyze ($K_{cat}$) the RNA substrate. However, RNA hydrolysis by conjugate 2 (FIG. 2A) leaves the conjugate bound to one of the cleavage products. This structure is stable under the reaction conditions; dissociation is inhibited and further activity by this conjugate is precluded. Hydrolysis by conjugate 1, however, results in cleavage at a site internal to the duplex region (FIG. 2B). The RNA cleavage products (bound to the DNA conjugate only by nine and eight base pairs) dissociate from the DNA conjugate under the reaction conditions, freeing the conjugate to bind and hydrolyze another RNA substrate.

Additional results were obtained from studies of the cleavage of substrate 3 by conjugate 1 and conjugate 4. The conjugates cleave substrate 3 at different sites as indicated by arrows; this study examined hydrolytic activities of the two conjugates when in competition with each other within the same reaction mixture.

```
Substrate 3 and conjugate 1:

3'                     v↓                        5'
A AAU AAA ACC UCU GAA GUA GAC ACU CGG CCC ACA AC       SEQ ID NO:4
       5' TGG AGA CT* CAT CTG TGA 3'
                   |
         DyTxO(CH2)3PO4

Substrate 3 and conjugate 4:

3'                        ↓                      5'
A AAU AAA ACC UCU GAA GUA GAC ACU CGG CCC ACA AC       SEQ ID NO:4
          5' DyTxO(CH2)3PO4TG TGA GCC GGG TGT TG 3'    SEQ ID NO:6
``` distributed into individual silanized microcentrifuge tubes, one tube per time point. All samples except the zero-time point were incubated at 37° C. using a PCR machine to control temperature. Samples were removed at selected time points, precipitated with ethanol, stored at −20° C., and subsequently separated by electrophoresis on a 20% denaturing polyacrylamide gel. The ratio of fragments produced by site-specific hydrolysis to intact substrate RNA was then quantitated using phosphorimaging techniques.

Hydrolysis of RNA substrate 3, expressed as the percentage of uncleaved RNA with time, is presented in FIG. 1. Under conditions having conjugate excess, the 5' derivatized DyTx-DNA conjugate 2 (■) displays greater activity than the internally-derivatized conjugate 1 (▲) with half-lives for hydrolysis of the RNA at ca. 4 h and 6 h, respectively. Under conditions having substrate excess (with excess cold RNA present), the apparent rate of the hydrolysis reactions decreases for both conjugates, since the excess unlabeled RNA competes with the labeled substrate for the DyTx-DNA conjugate. However, the order of hydrolysis activity changes for the two conjugates: In the reaction using the 5' derivatized DyTx-DNA conjugate 2 (♦, with 250 nM RNA), this inhibition is nearly complete, whereas in the reaction with internally-derivatized conjugate 1, (●, with 250 nM RNA), considerable RNA hydrolysis is still apparent, to the order of 30% cleavage after 24 h. This level of cleavage, 75 nM at 24 h (30% of 250 nM total RNA), represents three times the concentration of DyTx-DNA conjugate 1 in the reaction medium.

An explanation for the reversal of efficiency of RNA hydrolysis by the two conjugates under second-order conditions is that DyTx-DNA conjugate 1 is able to exhibit catalytic turnover, whereas DyTx-DNA conjugate 2 is not. This difference in catalytic performance is illustrated schematically in FIG. 2A and FIG. 2B. Both conjugates bind Buffered solutions were prepared containing both conjugates (25 nM of each DyTx-DNA conjugate 1 and 4, 50 mM HEPES, pH 7.5, 100 mM NaCl, 25 μM EDTA, 2 units/uL RNasin™ nuclease inhibitor (Promega Corporation), and 1 mM dithiothreitol, all concentrations are final). Substrate 5'-$^{32}$P-radiolabeled RNA (ca. 2 nM) and unlabeled RNA (25 nM, 100 nM, 250 nM, or 500 nM) were mixed and incubated for 5 min at 60° C., then added to conjugate solutions. The resulting mixtures were each distributed into individual silanized microcentrifuge tubes, one tube per time point for each RNA concentration. All samples except the zero-time point were incubated at 37° C. using a thermal cycler (Perkin-Elmer Model 2400) to control temperature. At selected time intervals, samples were removed from incubation, precipitated with ethanol, stored at −20° C., and subsequently separated by electrophoresis on a 20% denaturing polyacrylamide gel. The amounts of intact substrate RNA and cleavage products produced from site-specific hydrolysis by each conjugate were then quantitated using phosphorimaging techniques.

Figure 3:
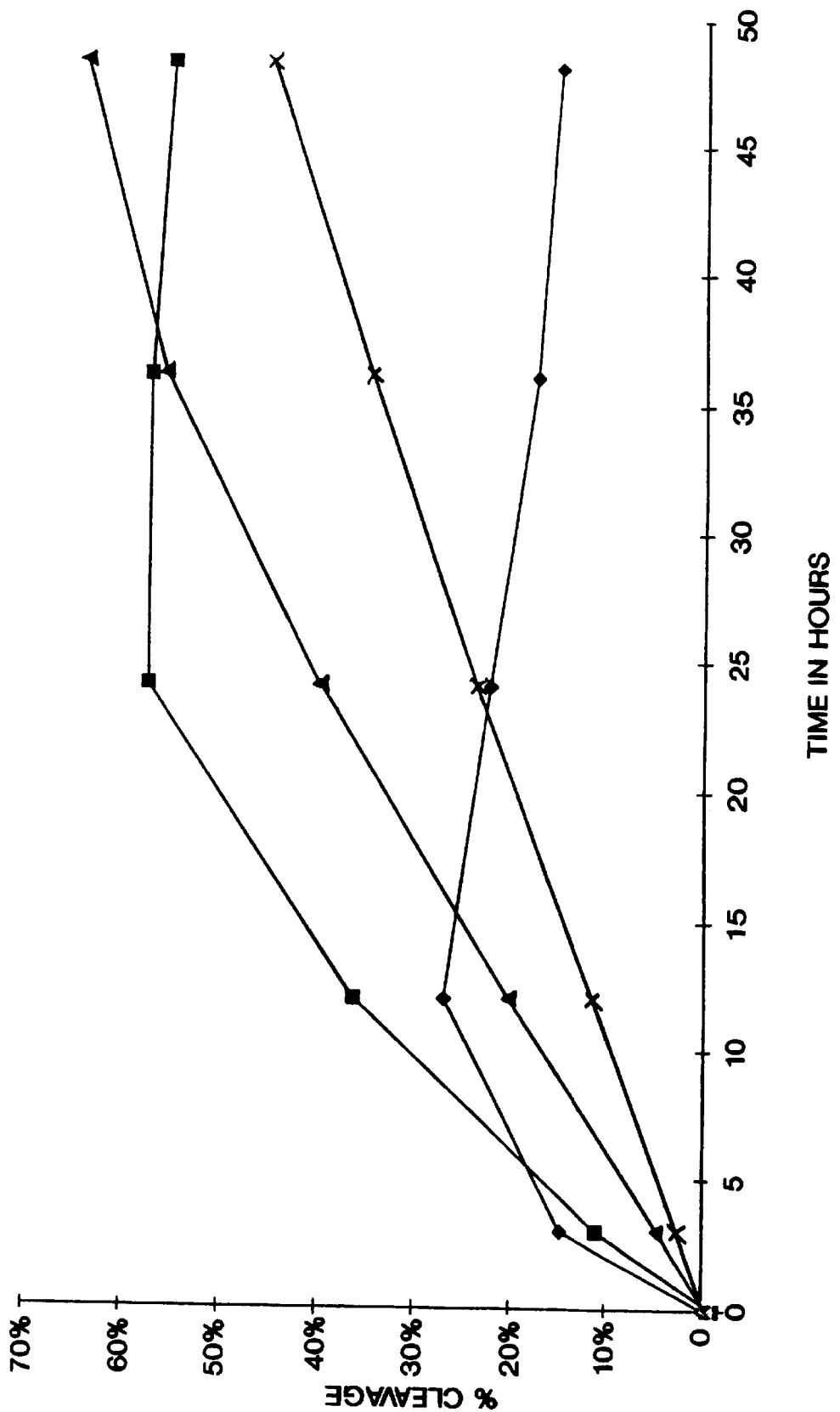
FIG. 3 shows site-specific hydrolysis of an RNA substrate by an internally-derivatized conjugate in the presence of an end-derivatized conjugate, the conjugates having binding specificity for the same substrate. See Example 4 for details. Symbols depict various concentrations of RNA substrate: ♦, 25 nM; ■, 100 nM; ▲, 250 nM; and X, 500 nM.
Figure 4:
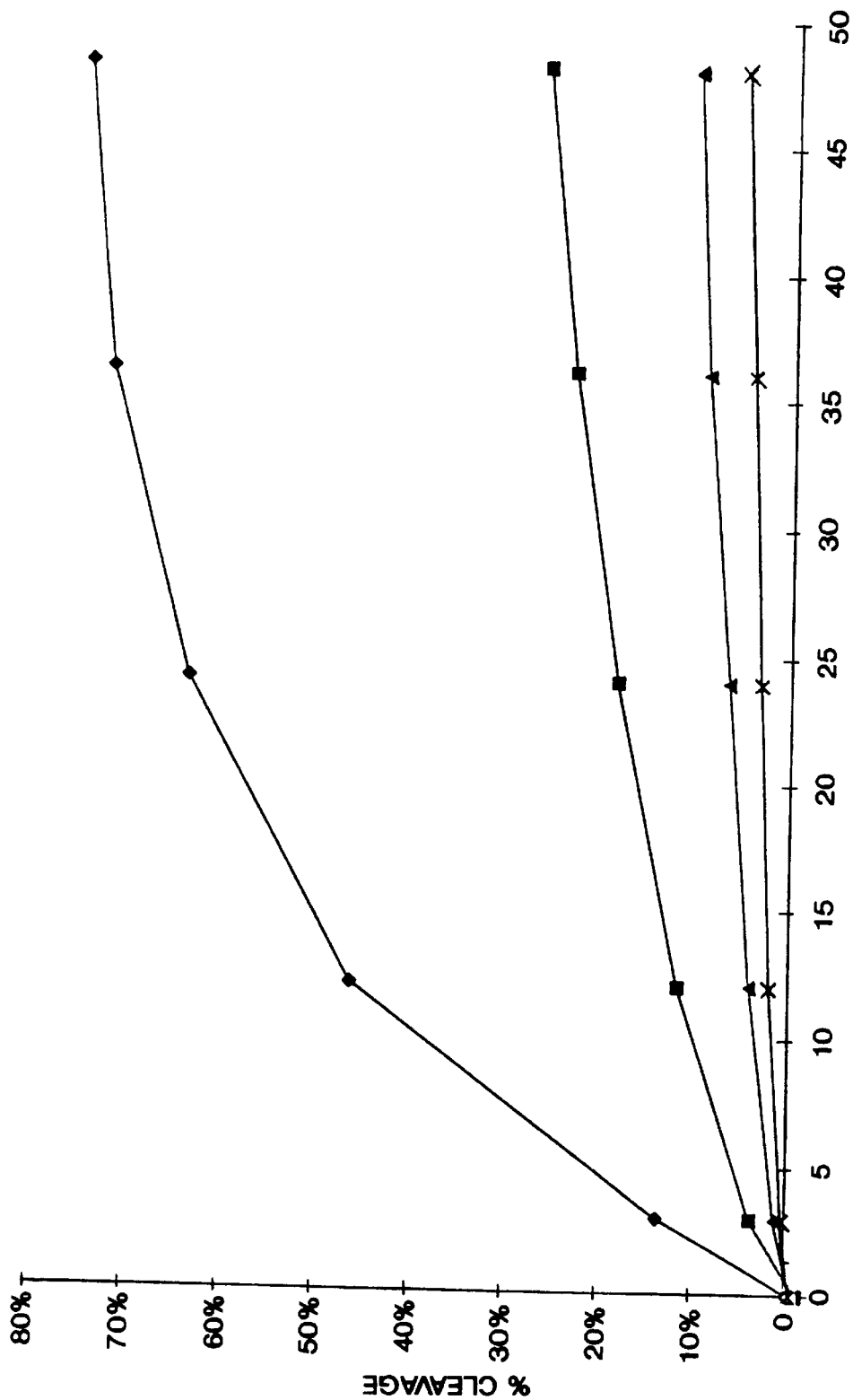
FIG. 4 shows site-specific hydrolysis of an RNA substrate by an end-derivatized conjugate in the presence of an internally-derivatized conjugate, the conjugates having binding specificity for the same substrate. See Example 4 for details. Symbols depict various concentrations of RNA substrate and are as in FIG. 3.

The extent of site-specific hydrolysis of RNA substrate 3 by conjugate 1, expressed as the percent of total RNA with time, is shown in FIG. 3. The extent of site-specific hydrolysis of substrate 3 by conjugate 4, expressed as the percent of total RNA with time, is shown in FIG. 4.

Under conditions where the substrate concentration of 25 nM is equal to each conjugate concentration, conjugate 4 cleaves the RNA more efficiently than conjugate 1, especially at later time points. This result is consistent with a cleavage product produced by conjugate 1 serving as a substrate for cleavage by conjugate 4.

At substrate concentrations greater than 25 nM, substrate is present in excess relative to the concentration of each conjugate. RNA cleaved, as calculated by the product of percent cleaved and total RNA, is approximately equivalent at these different concentrations using conjugate 4 (FIG. 4). Total cleavage by conjugate 4 approaches, but does not exceed, 25 nM (one equivalent of RNA). This observation is consistent with lack of turnover with this end-derivatized conjugate.

The percentage of RNA cleaved by conjugate 1, by contrast, is less affected by increased RNA concentrations (FIG. 3). At 100 nM RNA concentration, total RNA cleaved appears to reach a maximum of ca. 50 nM (50% cleavage), as a result of substrate depletion. At the two higher concentrations of substrate, the appearance of conjugate 1 RNA cleavage product is nearly linear over the course of the experiment. These reactions can be considered to occur under conditions having excess substrate. Further, there is an increase in the rate of total RNA cleavage at the higher substrate concentrations. At the highest concentration of RNA, about 23% cleavage is observed at 24 h, corresponding to 115 nM conjugate 1 cleavage product, or about four or five turnovers. After 48 h, about 45% RNA cleavage is seen corresponding to 225 nM conjugate 1 cleavage product or about 9 turnovers. By comparison, 5% cleavage of 5% nM substrate (25 nM product) was seen after 48 h by end-derivatized conjugate 4, indicating no turnover.

Catalytic activity demonstrating turnover under conditions having substrate excess using conjugate 1 has important implications for the use of texaphyrin metal complex-oligonucleotide conjugates within the context of antisense therapy. Such constructs would be expected to perform more effectively under conditions where the concentration of RNA target exceeds that of available conjugate, for example, conditions within the cellular milieu. Further, newly transcribed RNA is a potential substrate, even in the absence of further cellular uptake of the conjugate. Cellular hydrolytic cleavage activity would be prolonged for the internally-derivatized conjugates as compared to the end-derivatized conjugates.

EXAMPLE 5

Further Turnover Studies of Hydrolysis of RNA Using Texaphyrin Internally-Derivatized Oligonucleotide Conjugates The present example provides further studies of hydrolysis of RNA and turnover data obtained using texaphyrin internally-derivatized oligonucleotide conjugates. Conjugates were purified by reverse phase HPLC and preparative gel electrophoresis, and characterized by positive ion MALDI™ mass spectral analysis (Charles Evans & Assoc., Redwood City, Calif.).

The amount of cleavage of complementary RNA target 3 by DyTx-DNA conjugates 1 and 2 was evaluated under conditions of conjugate or substrate excess. Buffered solutions were prepared of each test species [50 nM DyTx-DNA conjugate, 50 nM HEPES, pH 7.5, 100 mM NaCl, 25 $\mu$M EDTA, 2 units/$\mu$L RNasin™ nuclease inhibitor (Promega Corporation, Madison, Wis.), and 1 mM dithiothreitol, all concentrations final]. To assay under conditions of excess conjugate, the substrate, 5'-$^{32}$P -radiolabeled RNA (ca. 2 nM), was incubated for 5 minutes at 60° C., and then added to the conjugate solutions. To assay under conditions of excess RNA, a mixture of 5'-$^{32}$P-radiolabeled RNA (ca. 2 nM) and unlabeled RNA (500 nM) substrate were incubated together for 5 minutes at 60° C., before adding to the conjugate solutions. The amount of site-specific RNA cleavage at 37° C. was determined as in Example 4. Under conditions of (>20-fold) conjugate excess, conjugates 2 and 1 displayed similar cleavage kinetics, with half-lives for RNA transesterification of ca. 2.4 hours and 2.2 hours being recorded for these two species, respectively. Addition of a 10-fold excess of substrate (to give 500 nM RNA), illustrates an important difference between these two species, namely, that one effects catalytic cleavage and the other does not. In particular, using the 5'-derivatized conjugate 2, ca. 5% of RNA is cleaved after 24 hours, whereas in the reaction with internally-derivatized conjugate 1, cleavage of 67% of the total RNA is observed under identical conditions. This level of cleaved RNA, 335 nM after 24 hours (67% of 500 nM total RNA), corresponds to a value that is 6.7 times the concentration of the DyTx-DNA conjugate 1 present in the reaction medium.

To further evidence this difference in reactivity, cleavage of 3 by 1 and by a 5'-derivatized DyTx-DNA conjugate which cleaves at an upstream site (designated conjugate 4) was monitored within the same reaction mixture. Due to the differing lengths of RNA produced upon cleavage by these conjugates, it was possible to examine the activities of the two types of conjugate while competing for the same substrate within the same reaction mixture. The amount of product formed by the internally derivatized conjugate under conditions where substrate depletion does not occur was about 10-fold greater than the amount of product formed by the 5'-end labeled conjugate in this competition study.

These data support the previous results showing that DyTx-DNA conjugate 1 is able to exhibit catalytic turnover, whereas the 5'-coupled DyTx-DNA conjugates 2 and 4 are unable to achieve catalytic turnover.

These results confirm that the different RNA cleaving activities displayed by the 5'-end and internally modified DyTx-DNA conjugates is an intrinsic property of the compounds and not, for example, a consequence of adventitious nuclease activity in the reaction medium.

An increase in the rate of RNA cleavage was observed by 1 at higher substrate concentration. Therefore, studies were carried out to examine whether internally modified DyTx-DNA conjugate 1 would exhibit saturation behavior upon titration with excess substrate. Values of $k_{cat}$, $K_M$ were derived from initial rate plots for conjugate 1, and also for conjugates in which the length of the antisense portion was truncated or extended by one base at each of the 5' and 3' ends, respectively (cf., Table 1).

TABLE 1

Initial Rate Data

| Conjugate | $k_{cat}$ (hour$^{-1}$)[a] | $K_M$ (nM)[a] |
| --- | --- | --- |
| 1 | 0.286 ± 0.057 | 20 ± 4 |
| 1 Truncated by 1 base at each end | 0.205 ± 0.004 | 69 ± 4 |
| 1 Extended by 1 base at each end | 0.215 ± 0.007 | 6 ± 2 |

[a]Average values from 3 independent determinations (± std. dev.)

The measured rates were found to vary between ca. 0.2–0.3 hour$^{-1}$, while the values of $K_M$ ranged from ca. 6–69 nM, depending on the length of the duplex formed upon hybridization with RNA substrate 3.

Further hydrolysis studies were carried out where the substrate RNA was designed such that a one or two base bulge or loop would be induced in the substrate upon hybridizing to the texaphyrin-oligonucleotide conjugate. The loop was either at or near (about 3–4 nucleotides) a position complementary to the site of attachment of texaphyrin to the conjugate. Hydrolysis of a one base loop was observed in the loop and at positions on the 5' side of the loop. Hydrolysis of a two base loop was observed when texaphyrin was attached to a ribonucleotide residue.

The effect of length of the oligonucleotide of the conjugate on hydrolysis and turnover was also studied. With the attachment site of the texaphyrin about in the middle of the conjugate, conjugate lengths of 16–26 nucleotides achieved hydrolysis and turnover of substrate RNA.

The effect of the position of attachment of the texaphyrin relative to the ends of the conjugate on hydrolysis and turnover was studied. When positioned 8 bases from the 5' end of a 24-mer conjugate, hydrolysis and turnover occurred. In contrast, a 5'-modified 15-mer conjugate designed to cleave the RNA at the same position demonstrated cleavage, but not turnover. This result suggests that strand displacement of the cleaved RNA by a new substrate is facilitated by the overhang portion of the conjugate.

Advantages of the present conjugate as compared to ribozymes for cleavage of RNA under biological conditions include the following: a DyTx-DNA conjugate such as 1 is in itself sufficient for activity since the dysprosium(III) cation-derived "active site" is pre-programmed into the catalyst structure as a result of using a texaphyrin macrocycle; the rates of cleavage by hammerhead ribozymes, on the other hand, are cation-dependent and typically are measured in the presence of 10 mM free Mg(II), conditions that are likely not to occur in vivo; a DyTx-DNA conjugate such as 1 is structurally simpler than a ribozyme, needing only to be of sufficient length to enable specific recognition of its cognate RNA substrate; RNA-cleaving systems of shortened length would enable cellular uptake and are more readily prepared on a large-scale; and in contrast to ribozyme-based approaches, there is no requirement in the present conjugates to preserve ribonucleotide regions in the catalytic portion of the construct, therefore, the approach embodied in conjugate 1 is compatible with non-natural antisense backbones as potential therapeutic agents.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

We claim:

1. A conjugate comprising a texaphyrin metal complex bound to an internal linkage of an oligonucleotide or oligonucleotide analog, the conjugate having hydrolytic cleavage activity for ribonucleic acid.

2. A conjugate comprising a texaphyrin metal complex bound to an internal linkage of an oligonucleotide or oligonucleotide analog, the conjugate having hydrolytic cleavage activity for ribonucleic acid wherein the texaphyrin metal complex has the formula:

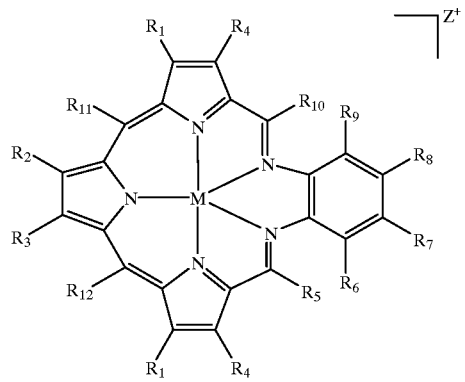

wherein

M is a divalent metal cation or a trivalent metal cation having catalytic activity for hydrolysis of ribonucleic acid;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, an oligonucleotide, an oligonucleotide analog, a catalytic group, an antibody, a steroid, a hormone, a peptide having affinity for a biological receptor, a sapphyrin molecule, or a couple that is coupled to an oligonucleotide, an oligonucleotide analog, a catalytic group, an antibody, a steroid, a hormone, a peptide having affinity for a biological receptor, or a sapphyrin molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple that is coupled to a saccharide, an oligonucleotide, an oligonucleotide analog, a catalytic group, an antibody, a steroid, a hormone, a peptide having affinity for a biological receptor, or a sapphyrin molecule;

at least one of $R_1$–$R_{12}$ is an oligonucleotide, oligonucleotide analog, or a couple that is coupled to an oligonucleotide or an oligonucleotide analog; and Z is an integer value less than or equal to 5.

3. The conjugate of claim 1 or 2 wherein the oligonucleotide has an internal ribose moiety, and the texaphyrin metal complex is bound at a 2' linkage of the ribose moiety.

4. The conjugate of claim 1 or 2 wherein the oligonucleotide analog has an internal branching linker in place of a nucleotide, and the texaphyrin metal complex is covalently bound to the internal branching linker.

5. The conjugate of claim 4 wherein the internal branching linker is a glycerol derivative.

6. The conjugate of claim 4 wherein the internal branching linker is an alkyl amino linker.

7. The conjugate of claim 1 or 2 having catalytic hydrolytic cleavage activity.

8. The conjugate of claim 1 or 2 wherein the texaphyrin metal complex is bound to an internal linkage of an oligonucleotide analog, and the oligonucleotide analog contains a derivative selected from the group consisting of methylphosphonate, phosphotriester, phosphorothioate, phosphoramidate, and 2' O-alkyl ribonucleotide.

9. The conjugate of claim 1 or 2 wherein the texaphyrin metal complex is bound to an internal linkage of an oligonucleotide analog, and the oligonucleotide analog contains a 2'-O-alkyl ribonucleotide.

10. A method of hydrolyzing ribonucleic acid under reaction conditions having excess substrate, the method comprising:
    contacting an excess of a ribonucleic acid with a conjugate of claim 1 or 2, said conjugate having at least partial sequence complementarity for said ribonucleic acid; and
    incubating said ribonucleic acid and conjugate for a time sufficient to hydrolyze a phosphate ester bond of said ribonucleic acid, allow turnover of the conjugate, and hydrolyze a second phosphate ester bond of said ribonucleic acid.

11. The conjugate of claim 1 wherein the texaphyrin metal complex has the formula:

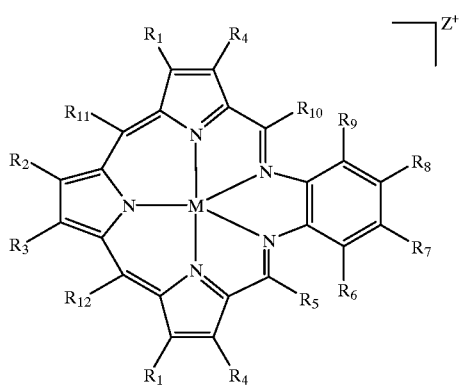

wherein
M is a divalent metal cation or a trivalent metal cation having catalytic activity for hydrolysis of ribonucleic acid;
$R_1-R_4$, $R_7$ and $R_8$ are independently hydrogen, halide, hydroxyl, alkyl, alkenyl, alkynyl, aryl, haloalkyl, nitro, formyl, acyl, hydroxyalkyl, oxyalkyl, oxyhydroxyalkyl, hydroxyalkenyl, hydroxyalkynyl, saccharide, carboxy, carboxyalkyl, carboxyamide, carboxyamidealkyl, amino, aminoalkyl, an oligonucleotide, an oligonucleotide analog, a catalytic group, an antibody, a steroid, a hormone, a peptide having affinity for a biological receptor, a sapphyrin molecule, or a couple that is coupled to an oligonucleotide, an oligonucleotide analog, a catalytic group, an antibody, a steroid, a hormone, a peptide having affinity for a biological receptor, or a sapphyrin molecule;

$R_6$ and $R_9$ are independently selected from the groups of $R_1-R_4$, $R_7$ and $R_8$, with the proviso that the halide is other than iodide and the haloalkyl is other than iodoalkyl;

$R_5$ and $R_{10}-R_{12}$ are independently hydrogen, alkyl, alkenyl, alkynyl, aryl, hydroxyalkyl, oxyalkyl, oxyhydroxyalkyl, hydroxyalkenyl, hydroxyalkynyl, carboxyalkyl, carboxyamide, carboxyamidealkyl, amino, aminoalkyl, or a couple that is coupled to a saccharide, an oligonucleotide, an oligonucleotide analog, a catalytic group, an antibody, a steroid, a hormone, a peptide having affinity for a biological receptor, or a sapphyrin molecule;

at least one of $R_1-R_{12}$ is an oligonucleotide, oligonucleotide analog, or a couple that is coupled to an oligonucleotide or an oligonucleotide analog; and Z is an integer value less than or equal to 5.

12. The conjugate of claim 2 or 11 wherein $R_1$, $R_2$, and $R_3$ are $CH_2CH_3$; $R_4$ is $CH_3$; $R_5$, $R_6$, $R_9$, $R_{10}$, $R_{11}$, and $R_{12}$ are H; $R_7$ is H or $OCH_3$, and $R_8$ is a couple that is coupled to an oligonucleotide or is a couple that is coupled to an oligonucleotide analog.

13. The conjugate of claim 12 wherein the couple is $O(CH_2)_3PO_4$ or $O(CH_2)_6PO_4$.

14. The conjugate of claim 2 or 11 wherein $R_1$ is $(CH_2)_2CH_2OH$; $R_2$ and $R_3$ are $CH_2CH_3$; $R_4$ is $CH_3$; $R_5$, $R_6$, $R_9$, $R_{10}$, $R_{11}$, and $R_{12}$ are H; $R_7$ is $OCH_3$, and $R_8$ is a couple that is coupled to an oligonucleotide or is a couple that is coupled to an oligonucleotide analog.

15. The conjugate of claim 14 wherein the couple is $O(CH_2)_3PO_4$ or $O(CH_2)_6PO_4$.

16. The conjugate of claim 2 or 11 wherein the trivalent metal cation is Eu(III), Gd(III), Tb(III), or Dy(III).

17. The conjugate of claim 1 or 2 wherein the oligonucleotide or oligonucleotide analog forms a region of local melting with the ribonucleic acid at or near a site of texaphyrin metal complex attachment.

18. A method for synthesizing the texaphyrin metal complex-oligonucleotide conjugate of claim 3, comprising:
    coupling a 2' hydroxyl of a ribonucleotide residue internal to the oligonucleotide to an amidite derivative of a texaphyrin metal complex.

19. A method for synthesizing the texaphyrin metal complex-oligonucleotide analog conjugate of claim 4, comprising:
    coupling the internal branching linker to an amidite derivative of a texaphyrin metal complex.

20. A method of hydrolyzing ribonucleic acid under reaction conditions having excess conjugate, the method comprising:
    contacting the ribonucleic acid with a conjugate of claim 1 or 2; and
    incubating the ribonucleic acid and the conjugate under reaction conditions having excess conjugate and for a time sufficient to hydrolyze a phosphate ester bond of the ribonucleic acid.

21. The method of claim 10 wherein the ribonucleic acid is messenger RNA or viral RNA.

22. The method of claim 20 wherein the texaphyrin metal complex is bound to an internal linkage of an oligonucleotide, the oligonucleotide has an internal ribose moiety, and the texaphyrin metal complex is bound at a 2' linkage of the ribose moiety.

23. The method of claim 10 wherein the texaphyrin metal complex is bound to an internal linkage of an oligonucleotide, the oligonucleotide has an internal ribose moiety, and the texaphyrin metal complex is bound at a 2' linkage of the ribose moiety.

24. The method of claim 20 wherein the texaphyrin metal complex is bound to an internal linkage of an oligonucleotide analog, the oligonucleotide analog has an internal branching linker in place of a nucleotide, and the texaphyrin metal complex is covalently bound to the internal branching linker.

25. The method of claim 10 wherein the texaphyrin metal complex is bound to an internal linkage of an oligonucleotide analog, the oligonucleotide analog has an internal branching linker in place of a nucleotide, and the texaphyrin metal complex is covalently bound to the internal branching linker.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:1:

TGGAGACTAC ATCTGTGA                                                          18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:2:

TGGAGACTTA ATCTGTGA                                                          18

(2) INFORMATION FOR SEQ ID NO:3:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:3:

CAACACCCGG CUCACAGAUG GAGUCUCCAA AAUAAA                                      36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:4:

CAACACCCGG CUCACAGAUG AAGUCUCCAA AAUAAA                      36

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CATCTGTGAG CCGGGTGTTG                      20

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:6:

TGTGAGCCGG GTGTTG                           16